United States Patent
Greaves et al.

(10) Patent No.: US 7,282,069 B2
(45) Date of Patent: Oct. 16, 2007

(54) CATIONIC DIAZO COMPOUNDS, COMPOSITIONS COMPRISING THEM AS DIRECT DYE, PROCESS FOR DYEING KERATIN FIBERS AND DEVICE THEREFOR

(75) Inventors: Andrew Greaves, Montevrain (FR); Hervé David, la Varenne Saint Hilaire (FR)

(73) Assignee: L'Oreal S.A., Paris (FR)

( * ) Notice: Subject to any disclaimer, the term of this patent is extended or adjusted under 35 U.S.C. 154(b) by 302 days.

(21) Appl. No.: 11/159,237

(22) Filed: Jun. 23, 2005

(65) Prior Publication Data

US 2006/0005327 A1    Jan. 12, 2006

Related U.S. Application Data

(60) Provisional application No. 60/588,048, filed on Jul. 15, 2004.

(30) Foreign Application Priority Data

Jun. 23, 2004    (FR) ................... 04 06869

(51) Int. Cl.
*A61K 7/13* (2006.01)

(52) U.S. Cl. .................. 8/405; 8/406; 8/407; 8/408; 8/410; 8/437; 8/571; 8/573; 8/574; 548/318.1; 548/400; 546/184; 546/249; 534/608

(58) Field of Classification Search ............ 8/405, 8/406, 407, 408, 410, 437, 571, 573, 574; 548/318.1, 400; 546/184, 249; 534/608
See application file for complete search history.

(56) References Cited

U.S. PATENT DOCUMENTS

| | | | |
|---|---|---|---|
| 3,151,106 A | 9/1964 | Tsang et al. | |
| 4,003,699 A | 1/1977 | Rose et al. | |
| RE30,199 E | 1/1980 | Rose et al. | |
| 4,563,191 A | 1/1986 | Hähnke et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,766,576 A | 6/1998 | Löwe et al. | |
| 5,792,221 A | 8/1998 | Lagrange et al. | |
| 5,852,179 A | 12/1998 | Dado | |
| 6,099,593 A | 8/2000 | Terranova et al. | |
| 6,284,003 B1 | 9/2001 | Rose et al. | |
| 6,645,258 B2 | 11/2003 | Vidal et al. | |
| 6,884,265 B2 | 4/2005 | Vidal et al. | |
| 2004/0244124 A1 | 12/2004 | Plos et al. | |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 044 059 | 1/1982 |
| EP | 0 714 954 | 6/1996 |
| EP | 0 770 375 | 5/1997 |
| EP | 1 133 976 | 9/2001 |
| FR | 2 586 913 | 3/1987 |
| FR | 2 692 572 | 12/1993 |
| FR | 2 733 749 | 11/1996 |
| FR | 2 750 048 | 12/1997 |
| GB | 1026978 | 4/1966 |
| GB | 1153196 | 5/1969 |
| JP | 2-19576 | 1/1990 |
| JP | 5-163124 | 6/1993 |
| WO | WO94/08969 | 4/1994 |
| WO | WO94/08970 | 4/1994 |
| WO | WO95/01772 | 1/1995 |
| WO | WO95/15144 | 6/1995 |
| WO | WO96/15765 | 5/1996 |
| WO | WO 02/078596 | 10/2002 |
| WO | WO 02/078596 A2 * | 10/2002 |
| WO | WO 02/100366 | 12/2002 |

OTHER PUBLICATIONS

STIC Search Report dated on May 10, 2007.*
Erwin Buncel and Sam-Rok Keum, "Studies of Azo and Azoxy Dyestuffs—16. Investigations of the Protonation and Tautomeric Equilibria of 4-(p'Hydroxyphenylazo)pyridine and Related Substrates," Tetrahedron, vol. 39, No. 7, pp. 1091-1101 (1983).
Mohammad H. Habibi, "Efficient Catalytic Oxidation of Primary Aromatic Amines to Azo Derivatives by Manganese (III) Tetraphenylporphyrin," J. Chem. Research, Issue. 10, pp. 648-649 (1998).
Ikenna Onyido and Collins I. Ubochi, "Heteroaromatic Azo-Activated Nucleophilic Substitutions. The Reaction of 4-(p-Methoxyphenylazo)pyridinium Methiodide with Piperidine in Dimethyl Sulphoxide," Heterocycles, vol. 26, No. 2, pp. 313-317 (1987).
Xiao-Yang Wang et al., "The Preparation of Symmetrical Azobenzenes from Anilines by Phase Transfer Catalyzed Method," Synthetic Communications, vol. 29, No. 13, pp. 2271-2276 (1999).
Siegfried Hünig and Gert Köbrich, "Synthase von 1-substituierten Pyridon-(4)-hydrazonen," Liebigs Ann. Chem., 617, pp. 180-202 (1958).
English language DERWENT abstract of EP 0 770 375, 1997.
English language DERWENT abstract of JP 2-19576, 1990.
English language DERWENT abstract of JP 5-163124, 1993.
French Search Report dated Feb. 15, 2005, for FR 0406872 (French Priority Application for co-pending U.S. Appl. No. 11/159,267).

(Continued)

*Primary Examiner*—Eisa Elhilo
(74) *Attorney, Agent, or Firm*—Finnegan, Henderson, Farabow, Garrett & Dunner LLP

(57) ABSTRACT

The present disclosure relates to cationic diazo compounds chosen from those of formula (I) and the acid addition salts thereof: Dye1-LK-Dye2 (I); and to dye compositions comprising the the compounds as direct dye, and also to a process for dyeing keratin fibers using this composition and a multi-compartment device.

27 Claims, No Drawings

OTHER PUBLICATIONS

French Search Report dated Feb. 16, 2005, for FR 0406871 (French Priority Application for co-pending U.S. Appl. No. 11/159,154).

French Search Report dated Feb. 16, 2005, for FR 0406870 (French Priority Application for co-pending U.S. Appl. No. 11/159,242).

French Search Report dated Feb. 16, 2005, for FR 0406869 (French Priority Application for co-pending U.S. Appl. No. 11/159,237, the present application).

Co-pending U.S. Appl. No. 11/159,267, Title: Cationic Diazo Compounds Compositions Comprising Them As Direct Dyes, Process for Dyeing Keratin Fibers and Device Therefor, Inventors: Andrew Greaves et al., filed Jun. 23, 2005.

Co-pending U.S. Appl. No. 11/159,154, Title: A Cationic Diazo Compound, Compositions Comprising At Least One Cationic Diazo Compound As Direct Dye, A Process for Dyeing Keratin Fibers and Device Therefor, Inventors: Andrew Greaves et al., filed Jun. 23, 2005.

Co-pending U.S. Appl. No. 11/159,242, Title: Cationic Diazo Compounds, Compositions Comprising Them As Direct Dye, Process for Dyeing Keratin Fibers and Device Therefor, Inventors: Andrew Greaves et al., filed Jun. 23, 2005.

* cited by examiner

CATIONIC DIAZO COMPOUNDS, COMPOSITIONS COMPRISING THEM AS DIRECT DYE, PROCESS FOR DYEING KERATIN FIBERS AND DEVICE THEREFOR

This application claims benefit of U.S. Provisional Application No. 60/588,048, filed Jul. 15, 2004, the contents of which are incorporated herein by reference. This application also claims benefit of priority under 35 U.S.C. § 119 to French Patent Application No. 04/06869, filed Jun. 23, 2004, the contents of which are also incorporated by reference.

The present disclosure relates to cationic diazo compounds of particular formulae, to dye compositions comprising such compounds as direct dyes in a medium that is suitable for dyeing keratin fibers, and also to a process for dyeing keratin fibers using this composition and a multi-compartment device.

It is known practice to dye keratin fibers, for example, human keratin fibers such as the hair, with dye compositions containing direct dyes. These compounds are colored and coloring molecules with affinity for the keratin fibers. It is known practice, for example, to use direct dyes of the nitrobenzene type, anthraquinone dyes, nitropyridines and dyes of the azo, xanthene, acridine, azine or triarylmethane type.

These dyes are usually applied to the fibers, optionally in the presence of an oxidizing agent if it is desired to obtain simultaneous lightening of the fibers. Once the leave-in time has elapsed, the fibers are rinsed, optionally washed and dried.

The colorations resulting from the use of direct dyes are temporary or semi-permanent colorations. The nature of the interactions that bind the direct dyes to the keratin fiber, and their desorption from the surface and/or the core of the fiber, are believed to be responsible for their poor dyeing power and their poor relative resistance to washing or to perspiration in comparison with permanent dye colorations.

An additional difficulty may also arise, associated with the fact that in order to obtain a particular color, it may be necessary in most, if not all, cases to mix together several dyes. However, each dye does not have the same affinity for the fibers, which is reflected either by heterogeneous colorations or by changes in color over time, for example after washing the fibers one or more times, exposure to sunlight, etc.

Thus it would be desirable to provide direct dyes that do not have one or more of the drawbacks of the existing direct dyes. In particular, it would be desirable to provide direct dyes with which varied shades can be obtained without the problem of changing in color over time.

To overcome at least one of the drawbacks of the prior art, the present inventors disclose herein cationic diazo compounds of formula (I) below, or the addition salts thereof with an acid:

Dye1-LK-Dye2     (I)

in which:

Dye1 and Dye2 are chosen such that the compound of formula (I) is not symmetrical, and are chosen from:

Dye 1:

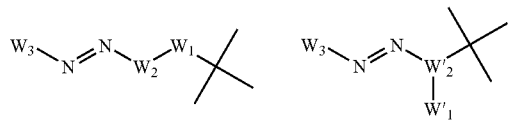

Dye 2:

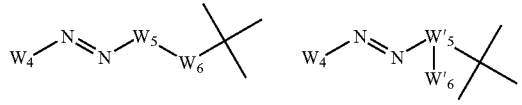

in which formulae:

$W_1$ and $W_6$, independently of each other, are chosen from —$NR_1$— and —O—, in which $R_1$ is chosen from a hydrogen atom and a saturated or unsaturated, aromatic or non-aromatic, optionally substituted $C_1$-$C_{20}$, for example $C_1$-$C_{16}$, hydrocarbon-based chain, which can form at least one optionally substituted 3- to 7-membered carbon-based ring, optionally interrupted with at least one hetero atom or with at least one group bearing at least one hetero atom, chosen from, for instance, oxygen and nitrogen;

$W'_1$ and $W'_6$, independently of each other, are chosen from groups —$NR'_1R'_2$ and —$OR'_3$, in which $R'_1$, $R'_2$ and $R'_3$, independently of each other, are chosen from hydrogen atoms and saturated or unsaturated, aromatic or non-aromatic, optionally substituted $C_1$-$C_{20}$, for example, $C_1$-$C_{16}$, hydrocarbon-based chains, which can form at least one optionally substituted 3- to 7-membered carbon-based ring, optionally interrupted with at least one hetero atom or with at least one group bearing at least one hetero atom, chosen, for instance, from oxygen and nitrogen; $R'_1$ and $R'_2$ may form, with the nitrogen atom to which they are attached, an optionally substituted 5- or 7-membered heterocycle optionally comprising another nitrogen or non-nitrogen hetero atom;

wherein the radicals $R_1$ of $W_1$ and $W_6$, together or separately, may form, with all or part of the group LK and with the nitrogen atom to which each is attached, a saturated or unsaturated, aromatic or non-aromatic, optionally substituted 5- to 7-membered heterocycle;

wherein the radicals $R'_1$, $R'_2$ or $R'_3$ of $W'_1$ and $W'_6$, together or separately, may form, with all or part of the group LK and with the nitrogen or oxygen atom to which each is attached, a saturated or unsaturated, aromatic or non-aromatic, optionally substituted 5- to 7-membered heterocycle;

$W_2$, $W_5$, $W'_2$ and $W'_5$, independently of each other, are chosen from groups of formulae (a), (b), and (c) below:

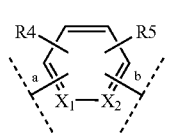

(a)

-continued

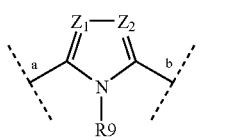
(b)

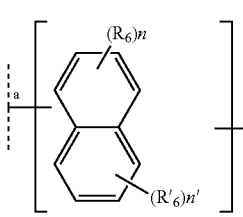
(c)

in which formulae:

$X_1$ is chosen from a nitrogen atom and a group $CR_7$;
$X_2$ is chosen from a nitrogen atom and a group $CR_8$;
$Z_1$ is chosen from a nitrogen atom and a group $CR_{10}$;
$Z_2$ is chosen from a nitrogen atom and a group $CR_{11}$;
$R_4$, $R_5$, $R_6$, $R'_6$, $R_7$, $R_8$, $R_{10}$ and $R_{11}$, independently of each other, are chosen from:
   linear or branched, saturated or unsaturated, aromatic or non-aromatic, optionally substituted $C_1$-$C_{16}$ hydrocarbon-based chains, which can form at least one optionally substituted 3- to 6-membered carbon-based ring, optionally interrupted with at least one hetero atom or with at least one group bearing at least one hetero atom, such as chosen from oxygen and nitrogen;
   a hydroxyl group,
   $C_1$-$C_4$ alkoxy groups,
   $C_2$-$C_4$ (poly)hydroxyalkoxy groups;
   alkoxycarbonyl groups (RO—CO—) in which R is a $C_1$-$C_4$ alkyl radical;
   alkylcarbonyloxy radicals (RCO—O—) in which R is a $C_1$-$C_4$ alkyl radical;
   an amino group,
   an amino group substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
   alkylcarbonylamino groups (RCO—NR—) in which the radicals R, independently of each other, are chosen from $C_1$-$C_4$ alkyl radicals;
   carbamoyl groups (($R)_2$N—CO) in which the radicals R, independently of each other, are chosen from a hydrogen atom and $C_1$-$C_4$ alkyl radicals;
   ureido groups (N(R)$_2$—CO—NR'—) in which the radicals R and R', independently of each other, are chosen from a hydrogen atom and $C_1$-$C_4$ alkyl radicals;
   sulfonamide groups (($R)_2$N—SO$_2$—) in which the radicals R, independently of each other, are chosen from a hydrogen atom and $C_1$-$C_4$ alkyl radicals;
   alkylsulfonylamino groups (RSO$_2$—NR'—) in which the radicals R and R', independently of each other, are chosen from a hydrogen atom and $C_1$-$C_4$ alkyl radicals;
   guanidinium groups ((R')$_2$N—C(=NH$_2^+$)—NR—) in which the radicals R and R', independently of each other, are chosen from a hydrogen atom and $C_1$-$C_4$ alkyl radicals;
   a nitro group;
   a cyano group;
   a halogen atom, such as chlorine or fluorine;
wherein $R_4$, $R_5$, $R_7$, $R_8$, $R_{10}$ and $R_{11}$ may be a hydrogen atom;
wherein $R_4$, $R_5$, $R_6$, $R'_6$, $R_7$, $R_8$, $R_{10}$ and $R_{11}$, independently of each other, may form, with, all or some of the groups $W'_1$ or $W'_6$ and, all or some of the groups $W_1$ or $W_6$, a saturated or unsaturated, aromatic or non-aromatic, optionally substituted 5- to 7-membered heterocycle;
a bond from $W'_2$ to $W'_1$ or to the group LK, or from $W'_5$ to $W'_6$ or to the group LK;
a is the bond from $W_2$, $W_5$, $W'_2$ or $W'_5$ to the azo group —N=N—;
b is the bond from $W_2$ to $W_1$, from $W_5$ to $W_6$, from $W'_2$ to $W'_1$ or to the group LK, or from $W'_5$ to $W'_6$ or to the group LK;
$R_9$ is chosen from:
   a hydrogen atom,
   a linear or branched, saturated or unsaturated, aromatic or non-aromatic, optionally substituted $C_1$-$C_{16}$ hydrocarbon-based chain, which can form at least one optionally substituted 3- to 7-membered carbon-based ring,
n and n' are chosen from integers and their sum is less than or equal to 6; with the proviso that when the sum n+n' is less than 6, each missing substituent is a hydrogen atom;
$W_3$ and $W_4$, independently of each other, are chosen from cationic heteroaromatic radicals chosen from one of the formulae (1) to (11) below:

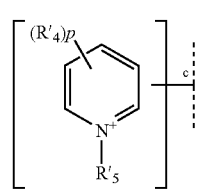
(1)

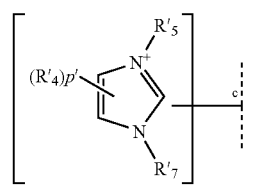
(2)

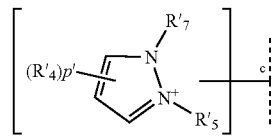
(3)

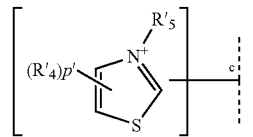
(4)

-continued

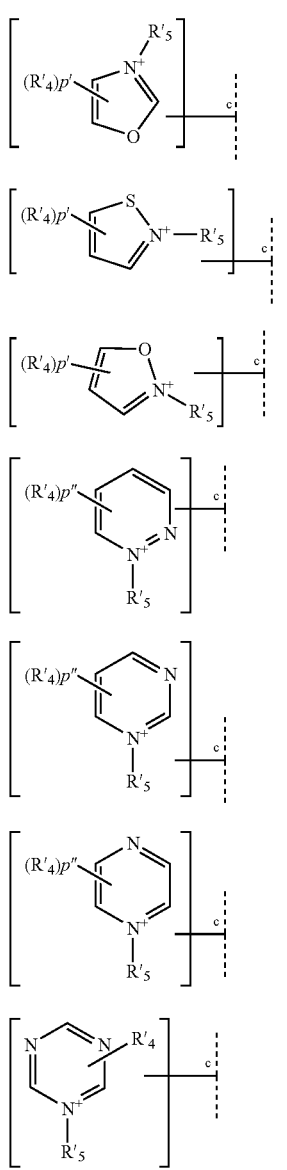

in which:
R'$_4$, which may be identical or different, substituting the main ring, is chosen from:
  linear or branched, saturated or unsaturated, aromatic or non-aromatic, optionally substituted $C_1$-$C_{16}$ hydrocarbon-based chains, which can form at least one 3- to 6-membered carbon-based ring, optionally interrupted with at least one hetero atom or with at least one group bearing at least one hetero atom, chosen, for example, from oxygen and nitrogen;
  a hydroxyl group,
  $C_1$-$C_4$ alkoxy groups,
  $C_2$-$C_4$ (poly)hydroxyalkoxy groups;
  alkoxycarbonyl groups (RO—CO—) in which R is chosen from $C_1$-$C_4$ alkyl radicals,
  alkylcarbonyloxy radicals (RCO—O—) in which R is a $C_1$-$C_4$ alkyl radical;
  an amino group,
  an amino group substituted with at least one $C_1$-$C_4$ alkyl radical, independently of each other, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
  alkylcarbonylamino groups (RCO—NR'—) in which the radical R is a $C_1$-$C_4$ alkyl radical and the radical R' is chosen from hydrogen and a $C_1$-$C_4$ alkyl radical;
  carbamoyl groups ((R)$_2$N—CO—) in which the radicals R are chosen from, independently of each other, a hydrogen atom and $C_1$-$C_4$ alkyl radicals;
  ureido groups (N(R)$_2$—CO—NR'—) in which the radicals R and R', independently of each other, are chosen from a hydrogen atom and $C_1$-$C_4$ alkyl radicals;
  sulfonamide groups ((R)$_2$N—SO$_2$—) in which the radicals R, independently of each other, are chosen from a hydrogen atom and $C_1$-$C_4$ alkyl radicals;
  alkylsulfonylamino groups (RSO$_2$—NR'—) in which the radicals R and R', independently of each other, are chosen from a hydrogen atom and $C_1$-$C_4$ alkyl radicals;
  guanidinium groups ((R')$_2$N—C(=NH$_2^+$)—NR—) in which the radicals R and R', independently of each other, are chosen from a hydrogen atom and $C_1$-$C_4$ alkyl radicals;
  a nitro group;
  a cyano group;
  a halogen atom, for example chlorine or fluorine;
  two radicals R'$_4$ borne by two adjacent carbon atoms of the main ring may optionally form an aromatic or non-aromatic, 5- or 6-membered secondary ring, optionally substituted with at least one entity chosen from hydrogen; hydroxyl groups; $C_1$-$C_4$ alkyl radicals; $C_1$-$C_4$ alkoxy radicals; $C_2$-$C_4$(poly)hydroxyalkoxy radicals; amino radicals; and amino radicals substituted with at least one $C_1$-$C_4$ alkyl radical, which may be identical or different, optionally bearing at least one hydroxyl group; for example, the secondary ring may be a 6-membered aromatic ring optionally substituted as indicated above;
R'$_5$, borne by the quaternized nitrogen atom, is a linear or branched, saturated or unsaturated, aromatic or non-aromatic, optionally substituted $C_1$-$C_{16}$ hydrocarbon-based chain, which can form an optionally substituted 3- to 7-membered carbon-based ring, optionally interrupted with at least one hetero atom or with at least one group bearing at least one hetero atom, chosen, for example, from oxygen, nitrogen and sulfur; wherein the radical R'$_5$ is such that the atom directly linked to the quaternized nitrogen atom is a carbon atom;
R'$_7$ is chosen from an optionally substituted $C_1$-$C_4$ alkyl radical; an optionally substituted phenyl radical; and an optionally substituted benzyl radical;
the bond c links the cationic radical defined by formulae (1) to (11) to the azo group; the bond may be on the main or secondary ring; for example, the bond c with the azo group may be on the main ring;
p is an integer ranging from 0 to 4,
p' is an integer ranging from 0 to 2 and
p'' is an integer ranging from 0 to 3;
with the proviso that when the main ring does not bear the maximum number of substituents, then the unsubstituted position(s) bear(s) a nitrogen atom and at least one of the two groups $W_3$ and $W_4$ is not an unsubstituted imidazolium group;

LK is a saturated or unsaturated, linear or branched, cyclic or non-cyclic, aromatic or non-aromatic, optionally substituted $C_2$-$C_{40}$, for example $C_2$-$C_{20}$, hydrocarbon-based chain, optionally interrupted with at least one hetero atom or group comprising at least one hetero atom, such as oxygen or nitrogen, wherein the group LK does not comprise any nitro, nitroso or peroxo groups or bonds; LK may end with a hetero atom or with a group bearing at least one hetero atom, such as oxygen or nitrogen if LK is linked to $W'_2$ or $W'_5$; LK may end with a group bearing at least one hetero atom chosen from —CO— and —$SO_2$— if LK is linked to $W_6$ or $W_1$;

wherein the electrical neutrality of the compounds is ensured by at least one cosmetically acceptable anion An.

A subject of the present disclosure is also dye compositions comprising, in a medium that is suitable for dyeing keratin fibers, such compounds or the addition salts thereof with an acid, as direct dyes.

The present disclosure also relates to a process for dyeing keratin fibers that comprises placing a composition according to the invention in contact with wet or dry fibers, for a time that is sufficient to obtain the desired effect.

Finally, the present disclosure relates to a multi-compartment device comprising, in a first compartment, the composition according to the invention, and, in a second compartment, an oxidizing composition.

It has been found that the compounds of formula Dye1-LK-Dye2 as defined above may show good fastness with respect to external agents such as shampoos, even when the keratin fiber is sensitized.

Furthermore, the compounds, which are dissymmetrical compounds, may allow access to colorations that are less chromatic than those obtained with symmetrical compounds.

Other characteristics and advantages of the present disclosure will emerge more clearly on reading the description and the examples below.

In the present text, unless otherwise indicated, the limits delimiting a range of values are included in that range.

Furthermore, Dye1 and Dye2 are such that the compound of formula (I) is not symmetrical; in other words, in the compound of formula (I), there is no axis or plane of symmetry passing through LK, the axis or plane of symmetry being coincident with or perpendicular to the main chain of LK.

For the purposes of the present disclosure, and unless otherwise indicated:

an alkyl radical is linear or branched, an alkyl radical or the alkyl part of a radical is said to be substituted when it comprises at least one substituent chosen from the following groups:
hydroxyl,
$C_1$-$C_4$ alkoxy,
$C_2$-$C_4$ (poly)hydroxyalkoxy,
amino,
amino substituted with at least one $C_1$-$C_4$ alkyl group, which may be identical or different, optionally bearing at least one hydroxyl group, the alkyl radicals possibly forming, with the nitrogen to which they are attached, a 5- or 6-membered heterocycle optionally comprising at least one other nitrogen or non-nitrogen hetero atom, an aryl or heteroaryl radical or the aryl or heteroaryl part of a radical is said to be substituted when it comprises at least one substituent borne by a carbon atom, chosen from
a $C_1$-$C_{16}$ and, for example, a $C_1$-$C_8$ alkyl radical, optionally substituted with at least one radical chosen from hydroxyl, $C_1$-$C_2$ alkoxy, $C_2$-$C_4$ (poly)hydroxyalkoxy, acylamino, and amino radicals substituted with two identical or different $C_1$-$C_4$ alkyl radicals, optionally bearing at least one hydroxyl group, or the two radicals possibly forming, with the nitrogen atom to which they are attached, a 5- to 7-membered and, for example, 5- or 6-membered, heterocycle, optionally comprising another nitrogen or non-nitrogen hetero atom;
a halogen atom such as chlorine, fluorine or bromine;
a hydroxyl group;
a $C_1$-$C_2$ alkoxy radical;
a $C_2$-$C_4$ (poly)hydroxyalkoxy radical;
an amino radical;
an amino radical substituted with one or two identical or different $C_1$-$C_4$ alkyl radicals optionally bearing at least one hydroxyl group, or amino with two optionally substituted $C_1$-$C_2$ alkyl radicals;
an acylamino radical (—NR—COR') in which the radical R is chosen from a hydrogen atom and a $C_1$-$C_4$ alkyl radical optionally bearing at least one hydroxyl group and the radical R' is a $C_1$-$C_2$ alkyl radical;
a carbamoyl radical (($R)_2$N—CO—) in which the radicals R, which may be identical or different, are chosen from a hydrogen atom and $C_1$-$C_4$ alkyl radicals optionally bearing at least one hydroxyl group;
an alkylsulfonylamino radical ($R'SO_2$—NR—) in which the radical R is chosen from a hydrogen atom and $C_1$-$C_4$ alkyl radicals optionally bearing at least one hydroxyl group and the radical R' is chosen from a $C_1$-$C_4$ alkyl radical and a phenyl radical;
an aminosulfonyl radical (($R)_2$N—$SO_2$—) in which the radicals R, which may be identical or different, are chosen from a hydrogen atom and $C_1$-$C_4$ alkyl radicals optionally bearing at least one hydroxyl group, the cyclic or heterocyclic part of a non-aromatic radical is said to be substituted when it comprises at least one substituent borne by a carbon atom, chosen from the following groups:
hydroxyl,
$C_1$-$C_4$ alkoxy,
$C_2$-$C_4$ (poly)hydroxyalkoxy,
alkylcarbonylamino((RCO—NR'—) in which the radical R' is chosen from a hydrogen atom and $C_1$-$C_4$ alkyl radicals optionally bearing at least one hydroxyl group and the radical R is chosen from $C_1$-$C_2$ alkyl radicals, and amino radicals substituted with two identical or different $C_1$-$C_4$ alkyl groups optionally bearing at least one hydroxyl group, the two alkyl radicals possibly forming, with the nitrogen atom to which they are attached, a 5- or 6-membered heterocycle optionally comprising at least one other nitrogen or non-nitrogen hetero atom.

As indicated previously, the present disclosure relates to compounds corresponding to the abovementioned formula (I).

In at least one embodiment, the compound of formula (I) Dye1-LK-Dye2 is such that the radicals $R_1$, $R'_1$, $R'_2$ and $R'_3$, independently of each other, are chosen from:
hydrogen atoms;

optionally substituted $C_1$-$C_6$ alkyl radicals;

aryl and arylalkyl radicals, such as phenyl or benzyl, the aryl part being optionally substituted;

the radicals $R_1$ of $W_1$ and $W_6$, together or separately, can form, with all or part of the group LK and with the nitrogen atom to which each is attached, a saturated or unsaturated, aromatic or non-aromatic, optionally substituted 5- to 7-membered heterocycle;

the radicals $R'_1$, $R'_2$ or $R'_3$ of $W'_1$ and $W'_6$, together or separately, can form, with all or part of the group LK and with the nitrogen or oxygen atom to which each is attached, a saturated or unsaturated, aromatic or non-aromatic, optionally substituted 5- to 7-membered heterocycle.

In accordance with one embodiment of the invention, the radicals $R_1$, $R'_1$, $R'_2$ and $R'_3$, which may be identical or different, are chosen from:

hydrogen atoms;

optionally substituted $C_1$-$C_3$ alkyl radicals, such as methyl, ethyl, 2-hydroxyethyl or 2-methoxyethyl;

phenyl radicals, optionally substituted with at least one radical chosen from hydroxyl, $C_1$-$C_2$ alkoxy and amino radicals, and amino radicals substituted with at least one $C_1$-$C_4$ groups optionally bearing at least one hydroxyl group;

the radicals $R_1$ of $W_1$ and $W_6$, or the radicals $R'_1$, $R'_2$ and $R'_3$ of $W'_1$ and $W'_6$, can form, with the nitrogen or oxygen atom for $R'_3$ to which each is attached and all or part of the group LK, a 5- to 7-membered heterocycle of pyrrolidine, piperidine, piperazine or homopiperazine type optionally substituted with at least one radical chosen from methyl, hydroxyl, amino and (di)methylamino radicals.

According to another embodiment, the radicals $R_1$, $R'_1$, $R'_2$ and $R'_3$, which may be identical or different, are chosen from:

hydrogen atoms;

radicals chosen from methyl, ethyl and 2-hydroxyethyl radicals;

phenyl radicals, optionally substituted with a radical chosen from hydroxyl, methoxy, amino, (di)methylamino and (di)(2-hydroxyethyl)amino radicals;

the radicals $R_1$ of $W_1$ and $W_6$, or the radicals $R'_1$, $R'_2$ and $R'_3$ of $W'_1$ and $W'_6$, can form, with the nitrogen or oxygen atom for $R'_3$ to which each is attached and all or part of the group LK, a 5- to 7-membered heterocycle such as pyrrolidine, 3-hydroxypyrrolidine, 3-dimethylaminopyrrolidine, piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine or 1-methyl-1,4-perhydrodiazepine.

The radicals $R_4$, $R_5$, $R_6$, $R'_6$, $R_7$, $R_8$, $R_{10}$ and $R_{11}$, which may be identical or different, are chosen from, in at least one embodiment:

hydrogen atoms for $R_4$, $R_5$, $R_7$, $R_8$, $R_{10}$ and $R_{11}$;

optionally substituted $C_1$-$C_{16}$ and for example $C_1$-$C_8$ alkyl radicals;

halogen atoms such as chlorine, fluorine or bromine;

hydroxyl groups;

$C_1$-$C_2$ alkoxy radicals;

$C_2$-$C_4$ (poly)hydroxyalkoxy radicals;

amino radicals;

amino radicals substituted with one or two $C_1$-$C_4$ alkyl radicals, which may be identical or different, optionally bearing at least one hydroxyl or $C_1$-$C_4$ dialkylamino group;

alkylcarbonylamino radicals (RCO—NR'—) in which the radical R is a $C_1$-$C_4$ alkyl radical and the radical R' is chosen from hydrogen and $C_1$-$C_4$ alkyl radicals;

carbamoyl radicals ((R)$_2$N—CO—) in which the radicals R, which may be identical or different, are chosen from hydrogen and $C_1$-$C_4$ alkyl radicals optionally bearing at least one hydroxyl group;

alkylsulfonylamino radicals (R'SO$_2$—NR—) in which the radical R is chosen from hydrogen and $C_1$-$C_4$ alkyl radicals optionally bearing at least one hydroxyl group, and the radical R' is a $C_1$-$C_4$ alkyl radical;

aminosulfonyl radicals ((R)$_2$N—SO$_2$—) in which the radicals R, which may be identical or different, are chosen from hydrogen and $C_1$-$C_4$ alkyl radicals optionally bearing at least one hydroxyl group;

a bond from $W'_2$ to $W'_1$ or to the group LK, or from $W'_5$ to $W'_6$ or to the group LK.

For example, the radicals, which may be identical or different, can be chosen from:

hydrogen atoms for $R_4$, $R_5$, $R_7$, $R_8$, $R_{10}$ and $R_{11}$;

$C_1$-$C_4$ alkyl radicals optionally substituted with at least one radical chosen from hydroxyl and acylamino radicals, and amino radicals substituted with two identical or different $C_1$-$C_2$ alkyl radicals, optionally bearing at least one hydroxyl group, or a $C_1$-$C_2$ alkoxy radical;

amino radicals;

amino radicals substituted with one or two identical or different $C_1$-$C_2$ alkyl radicals, optionally bearing at least one hydroxyl group;

acylamino radicals;

carbamoyl radicals;

sulfonylamino radicals;

hydroxyl radicals;

$C_1$-$C_2$ alkoxy radicals;

a bond from $W'_2$ to $W'_1$ or to the group LK, or from $W'_5$ to $W'_6$ or to the group LK.

According to one embodiment, the radicals $R_4$, $R_5$, $R_6$, $R'_6$, $R_7$, $R_8$, $R_{10}$ and $R_{11}$, independently of each other, are chosen from:

hydrogen atoms for $R_4$, $R_5$, $R_7$, $R_8$, $R_{10}$ and $R_{11}$;

radicals chosen from methyl, ethyl, propyl, 2-hydroxyethyl, methoxy, ethoxy, 2-hydroxyethyloxy, 3-hydroxypropyloxy and 2-methoxyethyl radicals;

radicals chosen from sulfonylamino, amino, methylamino, dimethylamino, 2-hydroxyethylamino, 3-hydroxypropylamino and acylamino radicals and hydroxyl radicals;

chlorine atoms;

a bond from $W'_2$ to $W'_1$ or to the group LK, or from $W'_5$ to $W'_6$ or to the group LK.

As regards the radical $R_9$, it may be, for example, chosen from a hydrogen atom, $C_1$-$C_{15}$ alkyl radicals; $C_2$-$C_6$ monohydroxyalkyl radicals; $C_2$-$C_6$-polyhydroxyalkyl radicals; ($C_1$-$C_6$)alkoxy($C_2$-$C_6$)alkyl radicals; optionally substituted aryl radicals, such as phenyl; optionally substituted arylalkyl radicals, such as benzyl; $C_2$-$C_6$ amidoalkyl radicals; $C_2$-$C_6$ aminoalkyl radicals, the amine of which is substituted with two identical or different, optionally substituted $C_1$-$C_4$ alkyl radicals.

In at least one embodiment, $R_9$ is chosen from a hydrogen atom, $C_1$-$C_6$ alkyl radicals, $C_2$-$C_6$ monohydroxyalkyl radicals; $C_2$-$C_6$ polyhydroxyalkyl radicals; ($C_1$-$C_6$)alkoxy($C_2$-$C_6$)alkyl radicals; phenyl radicals optionally substituted with at least one entity chosen from chlorine atoms, hydroxyl groups, RCO—NH— groups in which R is chosen from $C_1$-$C_4$ alkyl radicals, and amino radicals substituted with two identical or different $C_1$-$C_4$ alkyl radicals; benzyl radicals; $C_1$-$C_6$ aminoalkyl radicals; $C_1$-$C_6$ aminoalkyl radicals in which the amine is substituted with two identical or different $C_1$-$C_4$ alkyl radicals.

According to one embodiment, $W_2$, $W_5$, $W'_2$ and $W'_5$, independently of each other, are chosen from a group of formula (a) or (c). According to this embodiment, $X_1$ is a group $CR_7$. Also according to this embodiment, $X_2$ is a group $CR_8$.

$R_4$, $R_5$, $R_6$, $R'_6$, $R_7$ and $R_8$, independently of each other, have the same meanings as above.

As regards the groups $W_3$ and $W_4$, these groups, independently of each other, may be chosen from heterocycles chosen from those of formulae (1), (2), and (3):

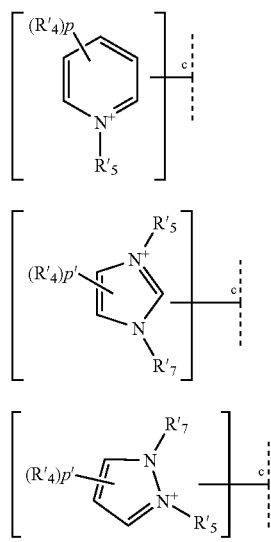

in which $R'_4$, $R'_5$, $R'_7$, p, p' and c are defined as above.

In at least one embodiment, $R'_5$ and $R'_7$ have the same definitions as $R_9$, with the exception of hydrogen.

Furthermore, at least one of the two groups $W_3$ or $W_4$ is not an unsubstituted imidazolium group.

In accordance with one embodiment of the present disclosure, the aromatic heterocyclic group is chosen from 2-imidazolium, 2-benzimidazolium, 2-pyridinium, 3-pyridinium, 4-pyridinium, 2-quinolinium, 4-quinolinium, 3-pyrazolium, 4-pyrazolium, 3-indazolium, 4-indazolium, 5-indazolium, 6-indazolium and 7-indazolium; on the condition that at least one of the two groups $W_3$ or $W_4$ does not represent an unsubstituted imidazolium group.

According to another embodiment of the present disclosure, the groups $W_3$ and $W_4$, which may be identical or different, are aromatic heterocycles chosen from 2-imidazolium, 2-pyridinium, 3-pyridinium, 4-pyridinium, 2-quinolinium, 4-quinolinium, 3-pyrazolium, 4-pyrazolium, 3-indazolium, 4-indazolium and 7-indazolium; on the condition that at least one of the two groups $W_3$ or $W_4$ does not represent an unsubstituted imidazolium group.

In one embodiment of formula (I), LK does not bear a cationic charge.

For example, LK may be chosen from linear, branched and cyclic, aromatic and non-aromatic $C_2$-$C_{20}$ alkyl chains:
- optionally interrupted with at least one hetero atom and/or group comprising at least one hetero atom, for instance —O—, —NR'—, —CO— or —$SO_2$—, or with a 5- or 6-membered heterocycle, comprising at least one nitrogen atom; on condition that there are no nitro, nitroso or peroxo groups or bonds in the group LK;
- optionally ending with a hetero atom or group bearing at least one hetero atom, such as oxygen or nitrogen, if LK is linked to $W'_2$ or $W'_5$;
- optionally ending with a group bearing at least one hetero atom chosen from —CO— and —$SO_2$— if LK is linked to $W_6$ or $W_1$;
- optionally substituted with at least one radical chosen from hydroxyl, $C_1$-$C_2$ alkoxy, $C_2$-$C_4$ (poly)hydroxyalkoxy, amino substituted with at least one linear or branched $C_1$-$C_2$ alkyl group optionally bearing at least one hydroxyl group.

For example, LK may be chosen from linear and branched $C_2$-$C_{20}$ alkyl chains optionally substituted with hydroxyl, or amino substituted with at least one linear or branched $C_1$-$C_4$ alkyl groups optionally bearing at least one hydroxyl group. Furthermore, when LK is linked to $W'_2$ or $W'_6$, LK may optionally end with at least one hetero atom or group comprising at least one hetero atom, for instance —O—, —NR'—, —CO— or —$SO_2$—.

According to another embodiment of the present disclosure, LK is chosen from $C_2$-$C_8$ linear and branched alkyl chains, optionally substituted with at least one radical chosen from hydroxyl, $C_1$-$C_2$ alkoxy and $C_1$-$C_2$ (di)alkylamino radicals or with a heterocycle. Furthermore, when LK is linked to $W'_2$ or $W'_5$, LK may optionally end with at least one hetero atom or group comprising at least one hetero atom, for instance —O—, —NR'—, —CO— or —$SO_2$—.

In accordance with one embodiment of the present disclosure, the compounds of formula (I) are chosen from those of the following formulae and the acid addition salts thereof:

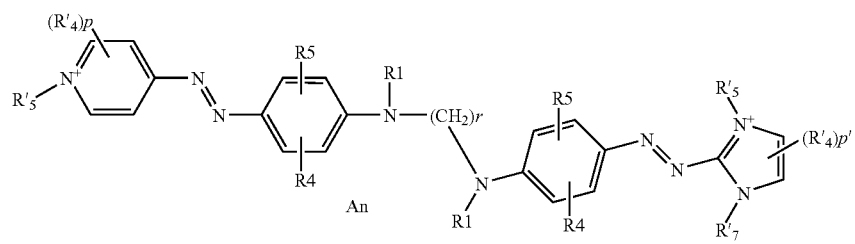

-continued
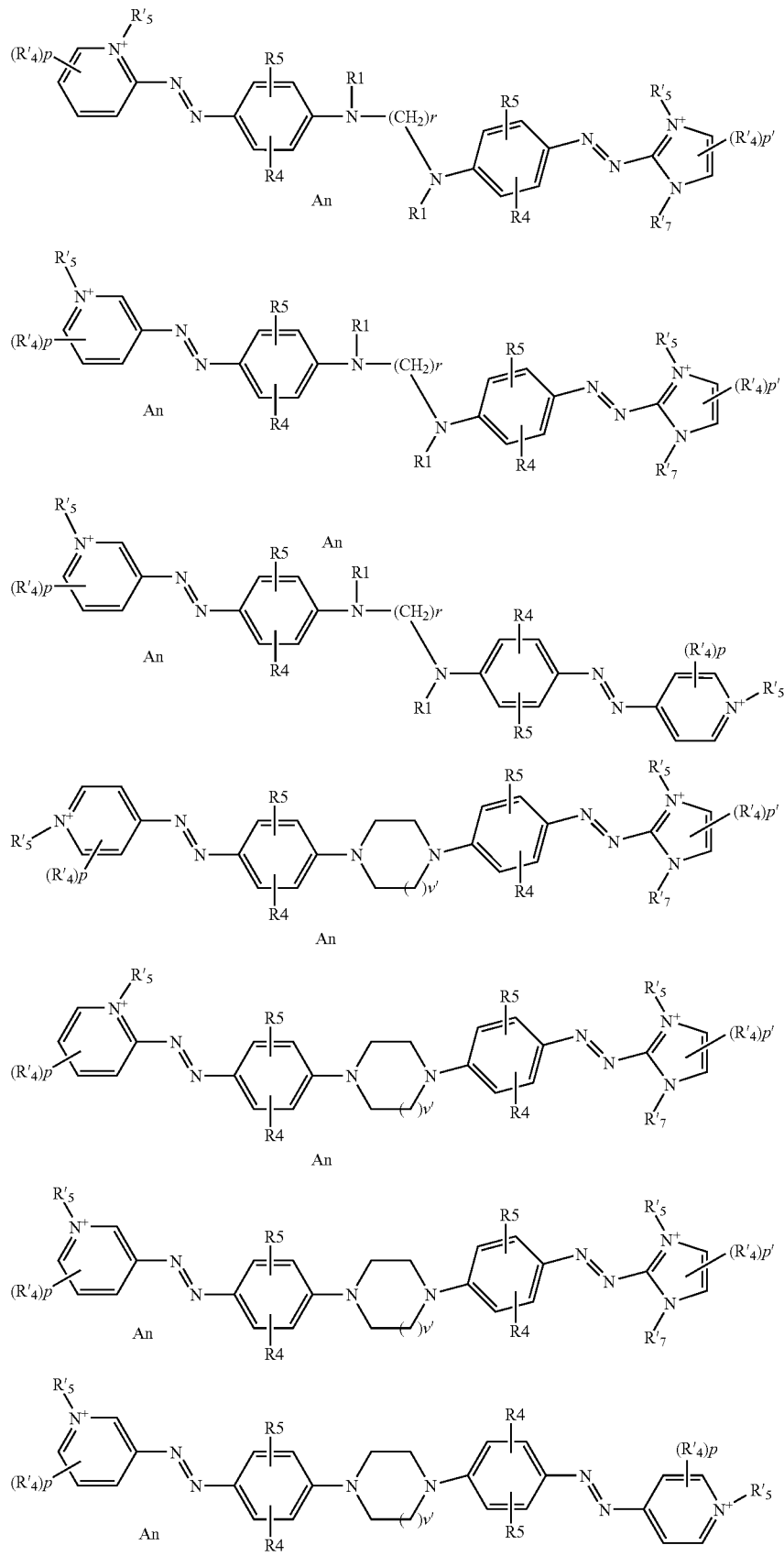

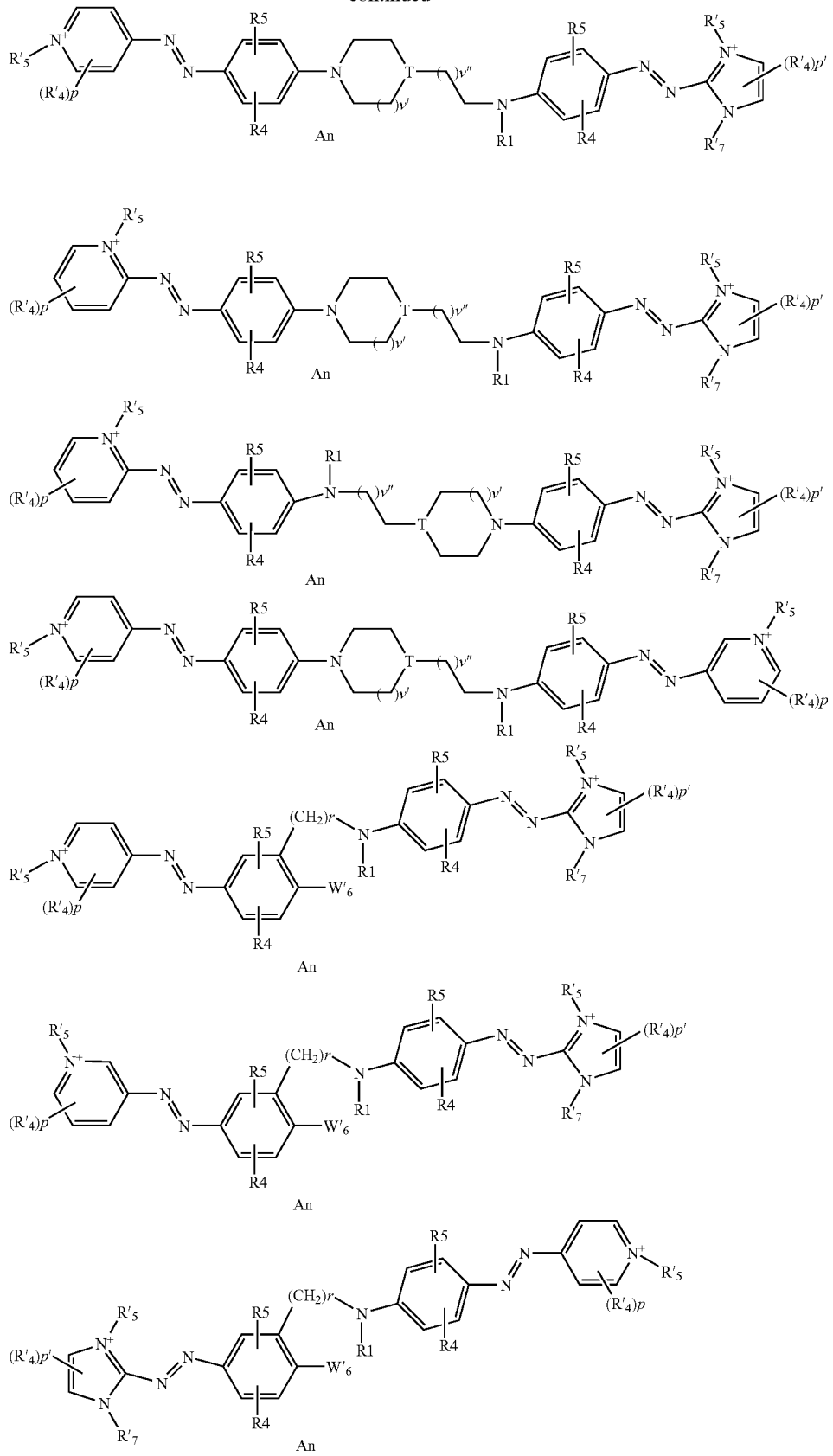

in which formulae $R_1$, $R_4$, $R_5$, $R'_4$, $R'_5$, $R'_7$, $W'_6$, p and p', which may be identical or different, have the same definitions as above;

r is an integer ranging from 1 to 10, such as from 1 to 5;

v' is an integer equal to 1 or 2

T is a carbon atom or a nitrogen atom v" is an integer equal to 1, 2 or 3 wherein the electrical neutrality of the molecule being respected by the presence of at least one cosmetically acceptable anions An.

The compounds of formula (I) comprise at least one cosmetically acceptable anion An chosen from halides, for instance chlorides or bromides; hydroxides; sulfates; hydrogen sulfates; carbonates, hydrogen carbonates; perchlorates; carboxylic acid salts, for instance acetates; citrates; tartrates; alkyl sulfates for which the linear or branched alkyl portion is chosen from $C_1$-$C_6$ alkyls, for instance methosulfate or ethosulfate ions; alkylsulfonates for which the linear or branched alkyl portion is chosen from $C_1$-$C_6$ alkyls; arylsulfonates for which the aryl portion, for instance phenyl, is optionally substituted with at least one $C_1$-$C_4$ alkyl radical.

The acid addition salts of the compounds of formula (I) can be, for example, halides, for instance chlorides or bromides, sulfates, alkyl sulfates for which the linear or branched alkyl portion is chosen from $C_1$-$C_6$ alkyls, for instance methosulfate or ethosulfate ions, hydrogen carbonates, perchlorates, carboxylic acid salts, for instance acetates; citrates; tartrates, alone or in combination.

These compounds may be, for instance, obtained from preparation processes described, for example, in U.S. Pat. No. 5,708,151, *J. Chem. Res., Synop.* (1998), (10), 648-649, U.S. Pat. Nos. 3,151,106 and 5,852,179, *Heterocycles*, 1987, 26 (2) 313-317, *Synth. Commun.* 1999, 29 (13), 2271-2276, and *Tetrahedron*, 1983, 39 (7), 1091-1101.

The present disclosure also relates to a dye composition comprising, in a medium that is suitable for dyeing keratin fibers, at least one direct dye compound chosen from those of formula (I) and the acid addition salts thereof with an acid.

The at least one direct dye compound of formula (I) can be present in the composition in an amount ranging from 0.001% to 20% by weight, for instance, from 0.01% to 10% by weight, such as from 0.05% to 5% by weight, relative to the total weight of the dye composition.

The composition according to the present disclosure may also comprise at least one oxidation base. The oxidation base may be chosen from the oxidation bases conventionally used in oxidation dyeing, for example ortho-phenylenediamines, para-phenylenediamines, double bases such as bis(phenyl) alkylenediamines, para-aminophenols, ortho-aminophenols and heterocyclic bases, the acid addition salts thereof, and also mixtures thereof.

Among the para-phenylenediamines that may be used, non-limiting mention may be made of, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the acid addition salts thereof.

Among the para-phenylenediamines, further non-limiting mention may be made of, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

Among the bis(phenyl)alkylenediamines that may be used, non-limiting mention may be made of, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

Among the para-aminophenols that may be used, non-limiting mention may be made of, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Among the ortho-aminophenols that may be used, non-limiting mention may be made of, for example, 2-aminophenol, 2-amino-5-methylphenol, 2-amino-6-methylphenol and 5-acetamido-2-aminophenol, and the acid addition salts thereof.

Among the heterocyclic bases that may be used, non-limiting mention may be made of, for example, pyridine derivatives, pyrimidine derivatives and pyrazole derivatives.

Among the pyridine derivatives that may be used, non-limiting mention may be made of the compounds described, for example, in British Patent Nos. GB 1 026 978 and GB 1 153 196, and 2,5-diaminopyridine, 2-(4-methoxyphenyl) amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Among the pyrimidine derivatives that can be used, non-limiting mention may be made of the compounds described, for example, in German Patent No. DE 2 359 399; Japanese Patent Nos. JP 88-169 571 and JP 05-163 124; European Patent No. EP 0 770 375 or International Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. FR-A-2 750 048 and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof and the tautomeric forms thereof, when a tautomeric equilibrium exists.

Among the pyrazole derivatives that may be used, non-limiting mention may be made of the compounds described in German Patent Nos. DE 3 843 892 and DE 4 133 957 and International Patent Application Nos. WO 94/08969 and WO 94/08970, French Patent Application No. FR-A-2 733 749, and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, and 3,5-diamino-4-(β-hydroxyethyl)amino-1-methylpyrazole, and the acid addition salts thereof.

The composition according to the present disclosure may also comprise at least one coupler conventionally used for dyeing keratin fibers. Among these couplers, non-limiting mention may be made of, for example, meta-phenylenediamines, meta-aminophenols, meta-diphenols, naphthalene-based couplers and heterocyclic couplers, the acid addition salts thereof, and also mixtures thereof.

Non-limiting examples of couplers that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene and the acid addition salts thereof.

In the composition of the present disclosure, the at least one coupler, when present, can be present in an amount ranging from 0.001% to 10% by weight, such as from 0.005% to 6% by weight, relative to the total weight of the dye composition. The at least one oxidation base, when present, can be present in an amount ranging, for example, from 0.001% to 10% by weight, such as from 0.005% to 6% by weight, relative to the total weight of the dye composition.

the acid addition salts that may be used in the context of the dye compositions of the present disclosure for the oxidation bases and couplers can be chosen from, for example, the hydrochlorides, hydrobromides, sulfates, citrates, succinates, tartrates, lactates, tosylates, benzenesulfonates, phosphates and acetates.

The composition according to the present disclosure may optionally comprise at least one additional direct dye other than the compounds of formula (I). This dye may be chosen from cationic and nonionic species.

Non-limiting examples of the at least one additional direct dye that may be mentioned include nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes and natural dyes, alone or as mixtures.

The at least one additional direct dye other than the compounds of formula (I) may be chosen from, for example, the following red or orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The at least one additional direct dye may also be chosen from yellow and green-yellow nitrobenzene direct dyes; non-limiting mention may be made, for example, of the compounds chosen from:
1-β-hydroxyethyloxy-3-methylamino-4-nitrobenzene,
1-(β-methylamino-2-nitro-5-(β,γ-dihydroxypropyl)oxybenzene,
1-(β-hydroxyethyl)amino-2-methoxy-4-nitrobenzene,
1-(O-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene, 1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Non-limiting mention may also be made of blue or violet nitrobenzene direct dyes, for instance:
1-(β-hydroxyethyl)amino-4-N,N-bis(β-hydroxyethyl)amino-2-nitrobenzene,
1-(γ-hydroxypropyl)amino-4, N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines of formula:

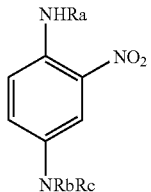

in which:
$R_b$ is chosen from $C_1$-$C_4$ alkyl radicals and β-hydroxyethyl, β-hydroxypropyl, and γ-hydroxypropyl radicals;
$R_a$ and $R_c$, which may be identical or different, are chosen from β-hydroxyethyl, β-hydroxypropyl, γ-hydroxypropyl and β,γ-dihydroxypropyl radicals, wherein at least one of the radicals $R_b$, $R_c$ or $R_a$ is a γ-hydroxypropyl radical and wherein $R_b$ and $R_c$ are not simultaneously a β-hydroxyethyl radical when $R_b$ is a γ-hydroxypropyl radical, such as those described in French Patent No. FR 2 692 572.

Among the azo direct dyes that may be used according to the present disclosure, non-limiting mention may be made of the cationic azo dyes described in International Patent Application Nos. WO 95/15144 and WO 95/01772, European Patent Application No. EP 714 954. Among these compounds, non-limiting mention may be made, for example, of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be used, non-limiting mention may be made of the following dyes described in the Color Index International 3rd edition:
Disperse Red 17,
Acid Yellow 9,
Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23,
Acid Orange 24, and
Disperse Black 9.

Non-limiting mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among the quinone direct dyes that may be used, non-limiting mention may be made of the following dyes:
Disperse Red 15,
Solvent Violet 13,
Acid Violet 43,
Disperse Violet 1,
Disperse Violet 4,
Disperse Blue 1,
Disperse Violet 8,
Disperse Blue 3,
Disperse Red 11,
Acid Blue 62,
Disperse Blue 7,
Basic Blue 22,
Disperse Violet 15,
Basic Blue 99,
and also the following compounds:
1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone, and
1,4-bis(β,γ-dihydroxypropylamino)anthraquinone.

Among the azine dyes that may be used, non-limiting mention may be made of: Basic Blue 17, and Basic Red 2.

Among the triarylmethane dyes that may be used according to the present disclosure, non-limiting mention may be made of:
Basic Green 1,
Acid Blue 9,
Basic Violet 3,
Basic Violet 14,
Basic Blue 7,
Acid Violet 49,
Basic Blue 26, and
Acid Blue 7.

Among the indoamine dyes that may be used according to the present disclosure, non-limiting mention may be made of:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

Among the dyes of tetraazapentamethine type that may be used according to the present disclosure, non-limiting mention may be made of the compounds given in the table below. An being defined as above:

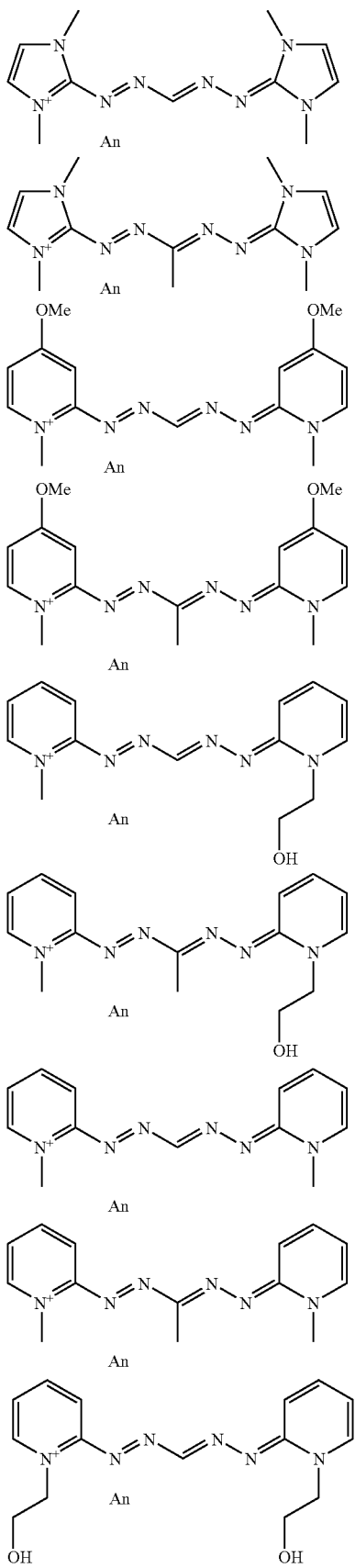

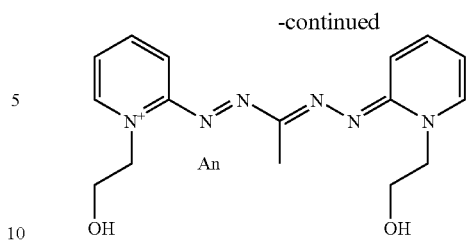

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin and apigenidin. Extracts or decoctions comprising these natural dyes may also be used, for instance henna-based poultices or extracts.

When the at least one additional direct dye is present in the composition, it can be present in an amount ranging from 0.001% to 20% by weight, relative to the weight of the composition, such as from 0.01% to 10% by weight, relative to the weight of the composition.

The medium that is suitable for dyeing, also known as the dye support, generally consists of water, or comprises a mixture of water and at least one organic solvent to dissolve the compounds that are not sufficiently water-soluble.

For example, the at least one organic solvent can be chosen from linear and branched, such as saturated monoalcohols and diols comprising from 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols and glycol ethers, for instance ethylene glycol monomethyl, monoethyl and monobutyl ether, propylene glycol and its ethers, for instance propylene glycol monomethyl ether, butylene glycol and dipropylene glycol; and also diethylene glycol alkyl ethers, such as of $C_1$-$C_4$, for instance diethylene glycol monoethyl ether or monobutyl ether, alone or as a mixture.

The at least one organic solvent, when present, can be present in an amount ranging from 1% to 40% by weight, such as from 5% to 30% by weight, relative to the total weight of the composition.

The dye composition in accordance with the present disclosure may also comprise at least one adjuvant chosen from the various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, for instance anionic, cationic, nonionic and amphoteric associative polymeric thickeners, antioxidants, penetrating agents, sequestering agents, fragrances, buffers, dispersants, conditioning agents, for instance silicones, which may or may not be volatile or modified, film-forming agents, ceramides, preserving agents and opacifiers.

The at least one adjuvant, when present, can be present in an amount for each adjuvant ranging from 0.01% to 20% by weight, relative to the weight of the composition.

Needless to say, a person skilled in the art will take care to select this or these optional additional compounds such that the beneficial properties intrinsically associated with the dye composition in accordance with the present disclosure are not, or are not substantially, adversely affected by the envisaged addition(s).

The pH of the dye composition in accordance with the present disclosure can range from 3 to 12, such as from 5 to 11. It may be adjusted to the desired value using acidifying or basifying agents usually used in the dyeing of keratin fibers, or alternatively using standard buffer systems.

Among the acidifying agents that may be used, non-limiting mention may be made of, for example, mineral or organic acids such as hydrochloric acid, orthophosphoric acid, sulfuric acid, carboxylic acids such as acetic acid, tartaric acid, citric acid and lactic acid, and sulfonic acids.

Among the basifying agents that may be used, non-limiting mention may be made of, for example, aqueous ammonia, alkaline carbonates, alkanolamines such as mono-ethanolamine, diethanolamine and triethanolamine and derivatives thereof, sodium hydroxide, potassium hydroxide and the compounds of the formula:

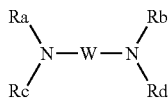

in which W is a propylene residue optionally substituted with a hydroxyl group or a $C_1$-$C_4$ alkyl radical; $R_a$, $R_b$, $R_c$ and $R_d$, which may be identical or different, are chosen from hydrogen atoms, $C_1$-$C_4$ alkyl radicals, and $C_1$-$C_4$ hydroxyalkyl radicals.

The dye composition according to the present disclosure may be in various forms, such as in the form of liquids, creams or gels, or in any other form that is suitable for dyeing keratin fibers, such as human hair.

The composition according to the present disclosure may also comprise at least one oxidizing agent. In this case, the composition is referred to as a ready-to-use composition.

As used herein, the term "ready-to-use composition" is understood to mean a composition intended to be applied immediately to the keratin fibers, i.e. it may be stored in unmodified form before use or may result from the extemporaneous mixing of two or more compositions.

The ready-to-use composition may also be obtained by mixing the composition according to the present disclosure with at least one oxidizing composition.

The at least one oxidizing agent may be any oxidizing agent conventionally used in the field. Thus, it may be chosen from, by way of non-limiting example, hydrogen peroxide, urea peroxide, alkali metal bromates, persalts such as perborates and persulfates, and also enzymes, among which non-limiting mention may be made of peroxidases, 2-electron oxidoreductases such as uricases, and 4-electron oxygenases, for instance laccases. For example, in one embodiment of the present disclosure, hydrogen peroxide is used.

The at least one oxidizing agent, when present, can be present in an amount ranging from 1% to 40% by weight, relative to the weight of the ready-to-use composition, such as from 1% to 20% by weight, relative to the weight of the ready-to-use composition.

The at least one oxidizing composition used may be, for example, an aqueous composition and may be in the form of a solution or an emulsion.

In one embodiment of the present disclosure, the composition free of oxidizing agent is mixed with about 0.5 to 10 weight equivalents of the oxidizing composition.

The pH of the ready-to-use composition can range from 4 to 12, such as from 7 to 11.5.

The pH of the ready-to-use composition may be adjusted using an acidifying or basifying agent chosen, for example, from those mentioned previously in the context of the description according to the present disclosure.

The present disclosure also relates to a dyeing process comprising applying a dye composition according to the present disclosure to wet or dry keratin fibers.

The application to the fibers of the dye composition comprising the at least one dye compound chosen from those of formula (I) and the addition salts thereof with an acid, optionally comprising at least one oxidation base optionally combined with at least one coupler, and optionally at least one additional direct dye, may be performed in the presence of at least one oxidizing agent.

The at least one oxidizing agent may be added to the composition comprising the at least one compound chosen from those of formula (I) and the optional oxidation bases, couplers and/or additional direct dyes, either at the time of use or directly onto the keratin fiber.

The oxidizing composition may also comprise at least one adjuvant chosen from the various adjuvants conventionally used in compositions for dyeing the hair and as defined above.

The pH of the oxidizing composition comprising the at least one oxidizing agent is such that, after mixing with the dye composition, the pH of the resulting composition applied to the keratin fibers ranges from 4 to 12, such as from 7 to 11.5. It may be adjusted to the desired value by means of acidifying or basifying agents usually used in the dyeing of keratin fibers and as defined above.

The composition that is finally applied to the keratin fibers may be in various forms, such as in the form of liquids, creams or gels or in any other form that is suitable for dyeing keratin fibers, such as human hair.

According to one embodiment, the composition according to the present disclosure is free of oxidation base and of coupler.

The composition applied may optionally comprise at least one oxidizing agent.

The composition is thus applied to the wet or dry keratin fibers and is then left for a period of leave-in time that is sufficient to obtain the desired coloration.

Whatever the variant adopted (with or without oxidizing agent), the period of leave-in time can range from few seconds to one hour, for instance, from 3 to 30 minutes.

The temperature at which the composition is left to act can range from 15° C. to 220° C., for instance from 15° C. to 80° C., such as from 15° C. to 40° C.

After the period of leave-in time, the composition is removed by rinsing with water, optionally followed by washing with a shampoo, and then optionally drying.

The present disclosure also relates to a multi-compartment device or dyeing "kit" in which at least one first compartment comprises at least one dye composition as disclosed herein, and at least one second compartment comprises at least one oxidizing composition. This device or "kit" may be equipped with an applicator for applying the desired mixture to the hair, such as the devices described in French Patent No. FR-2 586 913.

Other than in the operating examples, or where otherwise indicated, all numbers expressing quantities of ingredients, reaction conditions, and so forth used in the specification and claims are to be understood as being modified in all instances by the term. "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The examples that follow serve to illustrate the invention without, however, being limiting in nature.

EXAMPLES

Example 1

Synthesis of the Compound Below:

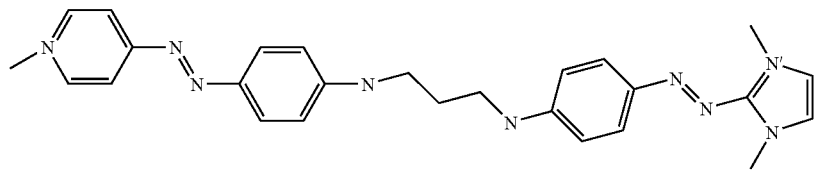

Counterion: MeSO4-/Cl- mixture

Synthetic Scheme

Compounds 1 and 2 were obtained according to the procedures described, respectively, in *Tetrahedron*, 1983, 39(7), 1091-1101, and U.S. Pat. No. 5,708,151

Procedure

Compound 2 (15.4 g), compound 1 (16.5 g) and water (150 ml) were placed in a three-necked flask. The mixture was heated to 95° C. (external temperature) with stirring.

After 3.5 hours, the heating was stopped and the mixture was allowed to cool to room temperature.

The solution was chromatographed to give the expected product.

After evaporation, a black solid (7.5 g) was obtained.

The NMR and mass spectra were in accordance with the structure of the expected product.

Example 1 of Dyeing:

The composition below was prepared:

| Ingredients | Amount |
|---|---|
| (50/50 C8/C10) Alkyl polyglucoside (2) as a buffered 60% aqueous solution | 12 g |
| Pure absolute ethanol | 20 g |
| Pure benzyl alcohol | 4 g |
| Polyethylene glycol 400 (8 EO) | 6 g |
| Demineralized water | qs 100 g |

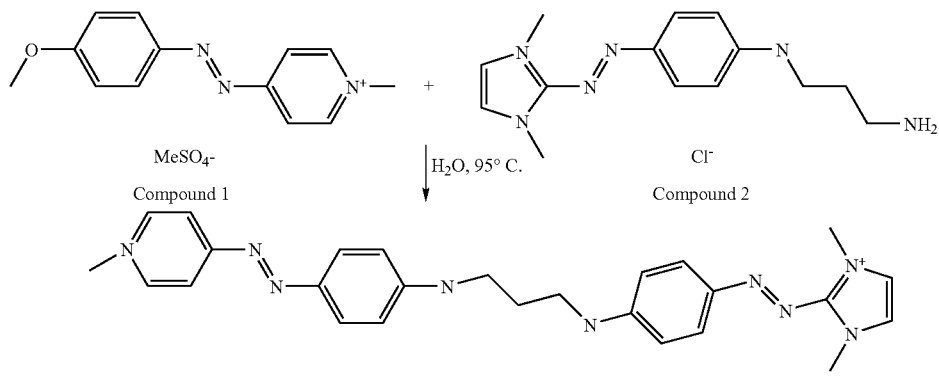

Counterion: MeSO4-/Cl- $5\times10^{-3}$ mol/l of compound obtained above were dissolved in this composition.

The composition thus obtained was applied to locks of hair comprising 90% white hair, at ambient temperature for a period of 30 minutes.

The locks were then rinsed, washed with a standard shampoo, rinsed again and dried.

A dark purple-black shade withstanding shampooing several times was obtained with the compound obtained above.

Example 2

Synthesis of the Compound [8]:

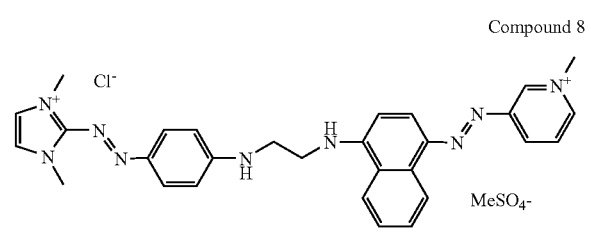

Compound 8

Synthetic Route

Step 1:

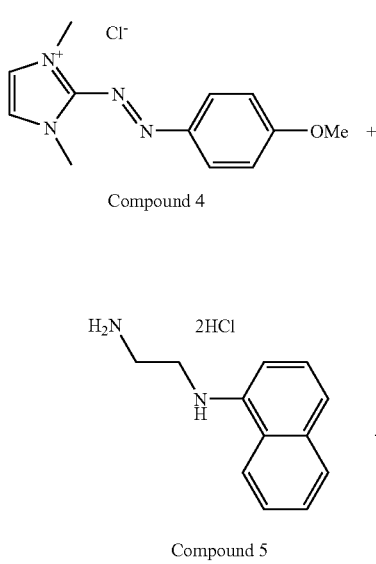

Compound [5] is commercially available.

In a three neck flask fitted with a mechanical stirrer and under a nitrogen atmosphere, [4] (5.52 g; 20.67 mmoles) was partially dissolved in isopropanol (90 ml), and then was heated at 60° C. A solution of [5] (7.7 g; 41.34 mmoles; 2 eq.) in isopropanol (20 ml) was added dropwise. The color of the reaction mixture became very dark red. The reaction mixture was heated at 60° C. overnight and then cooled down to room temperature.

Isopropanol (70 ml) was partially evaporated under vacuum, and a precipitate gradually formed.

The precipitate was filtered off, rinsed with isopropanol and dried under vacuum to give a green powder of [6] (8.15 g; 93%).

Standard analytical characterization was in agreement with the structure.

Step 2:

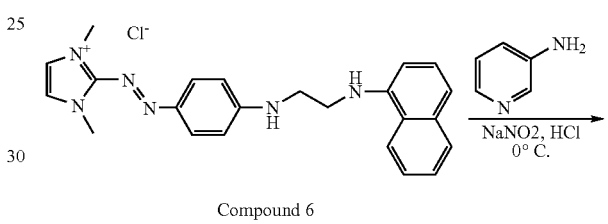

Compound 6

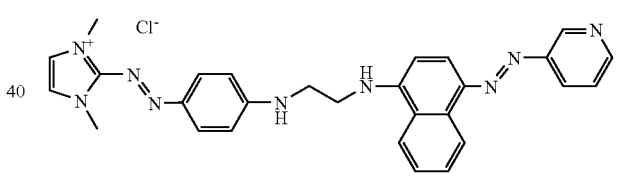

Compound 7

3-aminopyridine (0.232 g; 2.46 mmoles) was dissolved in 1.3 ml of 5N hydrochloric acid and 1.8 ml of water. The resulting solution was cooled to 0° C. and a solution of sodium nitrite (0.170 g; 2.46 mmoles) in 1.8 ml of water was added dropwise at 0-5° C. After 30 minutes the diazotization was complete.

A small amount of sulfamic acid was added. The so-obtained diazo solution was added dropwise at 0-5° C. to a solution of [6] (1 g; 2.38 mmoles; 0.97 eq.) in water (28 ml) and methanol (14 ml). The pH of the solution ranged from 4 to 5. The cooling bath was removed and the reaction mixture was stirred at room temperature for 2 hours. Its pH was adjusted to the range of 8 to 9 by dropwise addition of 40% aqueous sodium hydroxide.

A precipitate formed, was filtered off, rinsed with water and dried over $P_2O_5$ under vacuum overnight to give a red dark powder of [7] (1 g; 80%).

Standard analytical characterization was in agreement with the structure.

Step 3:

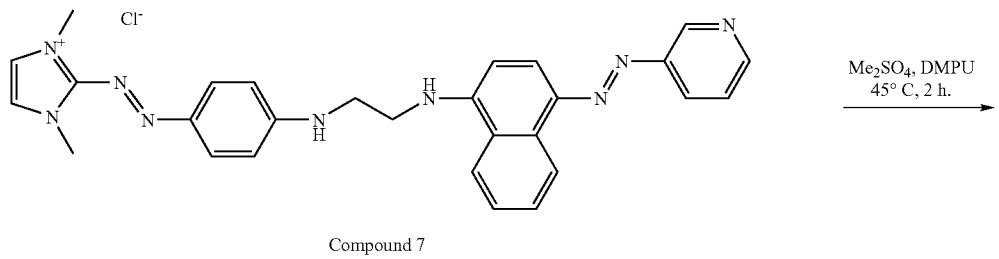

Compound 7

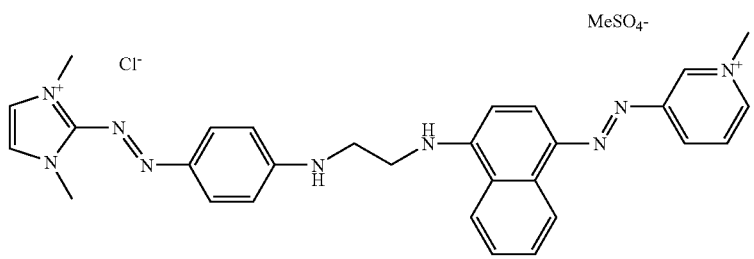

Compound 8

Compound [7] (0.250 g; 0.47 mmoles) was dissolved in 4 ml of DMPU and heated to 45-50° C. At 45-50° C., dimethyl sulfate (90 mg; 0.71 mmoles; 1.5 eq.) was added dropwise. The brown reaction mixture became darker. After 2 hours the quaternization was complete.

The reaction mixture was cooled down to room temperature and added with diethyl ether (8 ml) to give a dark precipitate. The reaction mixture was stirred for 15 min at room temperature and the precipitate was filtered, rinsed with diethyl ether. The wet solid was stirred with 4 ml of water to eliminate DMPU.

After filtration and drying over $P_2O_5$ under vacuum, a dark violet powder of [8] (0.14 g) was obtained.

Standard analytical characterization was in agreement with the structure.

Example 2 of Dyeing:

The following composition was prepared:

| Ingredients | Amount |
|---|---|
| Alkyl (C8/C10 50/50) polyglucoside (2) (60% buffered aqueous solution) | 12 g |
| Ethanol | 20 g |
| Benzyl alcohol | 4 g |
| Polyethyleneglycol 400 (8 EO) | 6 g |
| Water | qsp 100 g |

$5 \times 10^{-3}$ mol/l of the compound prepared before was solubilized into the above composition.

The resulting mixture was applied onto locks of hair with 90% of white hair, at ambient temperature for a period of 30 minutes.

The locks of hair were then rinsed, washed with a standard shampoo, rinsed again and dried.

The hair was dyed in a dull violet shade which resists to shampoos.

Example 3

Synthesis of the Compound 10:

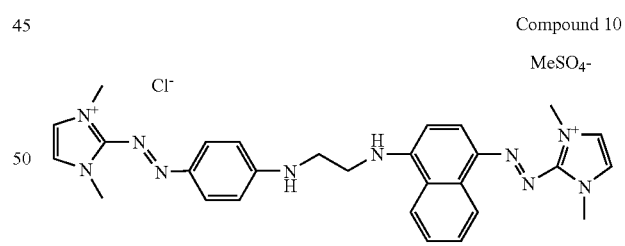

Compound 10

Synthetic Route

Step 1:

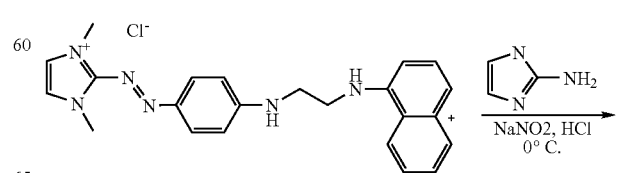

Compound 6

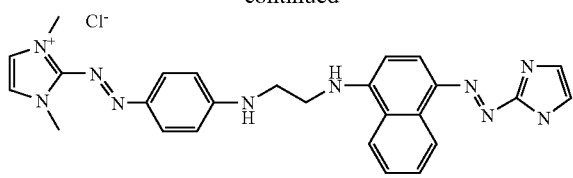

Compound 9

2-aminoimidazole sulphate salt is commercially available.

2-aminoimidazole sulphate salt (0.325 g; 2.46 mmoles) was dissolved in hydrochloric acid 37% (0.65 ml), acetic acid (0.65 ml) and water (3.25 ml). The resulting solution was cooled to 0° C. and a solution of sodium nitrite (0.170 g; 2.46 mmoles) in water (0.65 ml) was added dropwise at 0-5° C. After 30 minutes the diazotization was complete.

A small amount of sulfamic acid was added. The so-obtained diazo solution was added dropwise at 0-5° C. to a solution of [6] (1 g; 2.38 mmoles; 0.97 eq.) in water (20 ml). The pH of the solution was 1-2. The cooling bath was removed and the reaction mixture was stirred at room temperature for 2 hours. Its pH was adjusted to 8-9 by addition of 40% aqueous sodium hydroxide.

A precipitate formed, was filtered off, rinsed with water, diethyl ether and dried over $P_2O_5$ under vacuum overnight to give a dark red powder of [9] (1.03 g; 84%).

Standard analytical characterization was in agreement with the structure.

Step 2:

[9] (0.250 g; 0.48 mmoles) was dissolved in n-butanol (5 ml). Dimethyl sulfate (92 mg; 0.73 mmoles; 1.5 éq.) was added dropwise followed by potassium acetate (48 mg; 048 mmoles). The reaction mixture was heated at 80° C. for 4 hours. The dark pink reaction mixture became purple. After 4 hours the quaternization was complete.

The reaction mixture was cooled down to room temperature and a precipitate gradually formed. It was filtered, rinsed with n-butanol, acetone and dried under vacuum. A purple powder of [10] (0.27 g) was obtained.

Standard analytical characterization was in agreement with the structure.

Example 3 of Dyeing:

The following composition was prepared:

| Ingredients | Amount |
|---|---|
| Alkyl (C8/C10 50/50) polyglucoside (2) (60% buffered aqueous solution) | 12 g |
| Ethanol | 20 g |
| Benzyl alcohol | 4 g |
| Polyethyleneglycol 400 (8 EO) | 6 g |
| Water | qsp 100 g |

$5 \times 10^{-3}$ mol/l of the compound prepared before was solubilized into the above composition.

The resulting mixture was applied onto locks of hair with 90% of white hair, at ambient temperature for a period of 30 minutes.

The locks of hair were then rinsed, washed with a standard shampoo, rinsed again and dried.

The hair was dyed in a blackviolet shade which resists to shampoos.

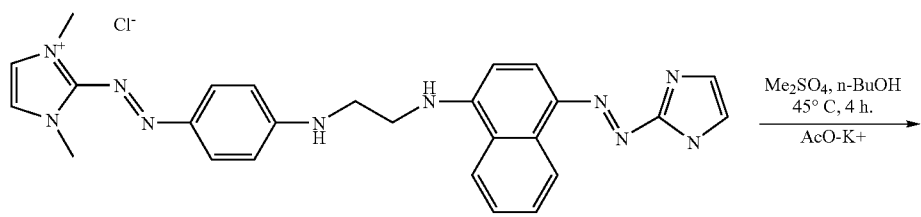

Compound 9

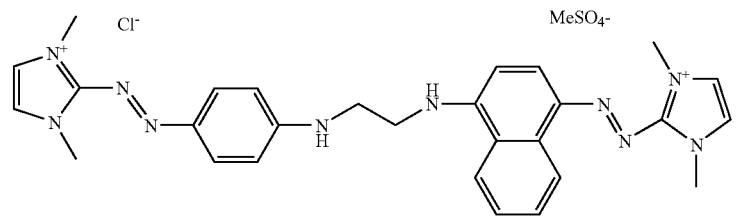

Compound 10

Example 4

Synthesis of the Compound [12]:

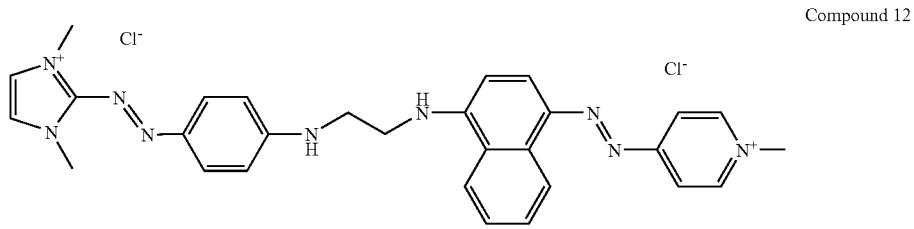

Compound 12

Synthetic Route

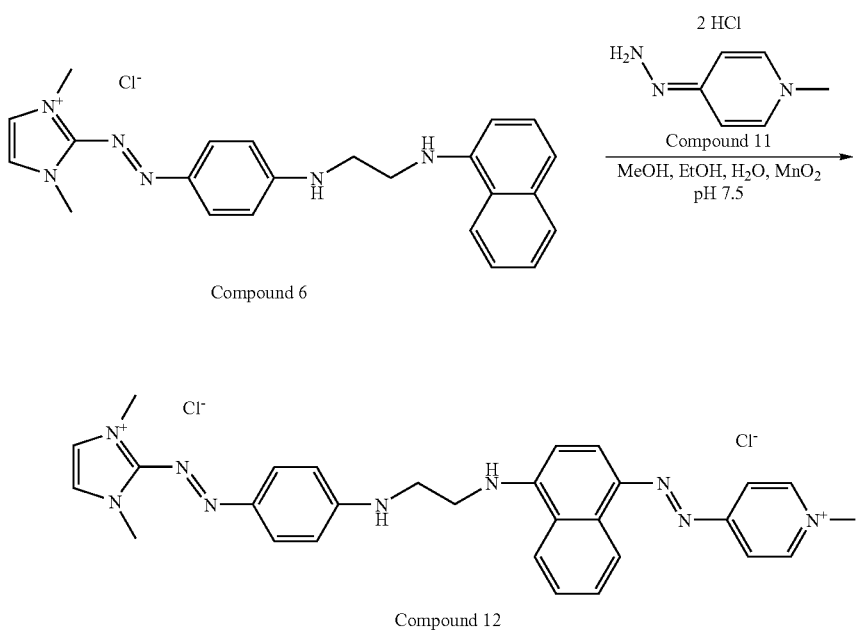

1-methylpyridin-4(1H)-one hydrazone [11] can be obtained using the reference: Hünig, Liebigs Ann. Chem., 617, 1958, 180-202.

[11] (0.196 g; 1 mmole) and [6] (0.420 g; 1 mmole) were dissolved in methanol (5 ml), ethanol (15 ml) and water (5 ml). The pH was adjusted to 7 by addition of 3% aqueous sodium hydroxide.

Manganese dioxide (0.870 g; 10 mmoles) was added slowly to the reaction mixture adjusting the pH to 7.5 by addition of 1N aqueous hydrochloride. The reaction mixture was stirred at room temperature for 12 hours.

The reaction mixture was beforehand filtered to remove manganese salts. 50 ml of acetone was added to the reaction mixture.

A precipitate formed, was filtered off, rinsed with isopropanol, and ethyl acetate and dried over $P_2O_5$ under vacuum overnight to give a black powder of [12]. Standard analytical characterization was in agreement with the structure.

Example 4 of Dyeing:

The following composition was prepared:

| Ingredients | Amount |
|---|---|
| Alkyl (C8/C10 50/50) polyglucoside (2) (60% buffered aqueous solution) | 12 g |
| Ethanol | 20 g |
| Benzyl alcohol | 4 g |
| Polyethyleneglycol 400 (8 EO) | 6 g |
| water | qsp 100 g |

$5 \times 10^{-3}$ mol/l of the compound prepared before was solubilized into the above composition.

The resulting mixture was applied onto locks of hair with 90% of white hair at ambient temperature for a period of 30 minutes.

The locks of hair were then rinsed, washed with a standard shampoo, rinsed again and dried.

The hair was dyed in a yellow brown shade which resisted shampooing.

Example 5

Synthesis of the Compound [14]:

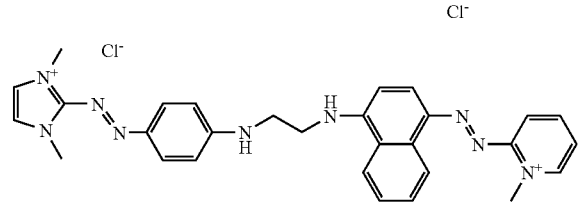

Compound 14

Synthetic Route

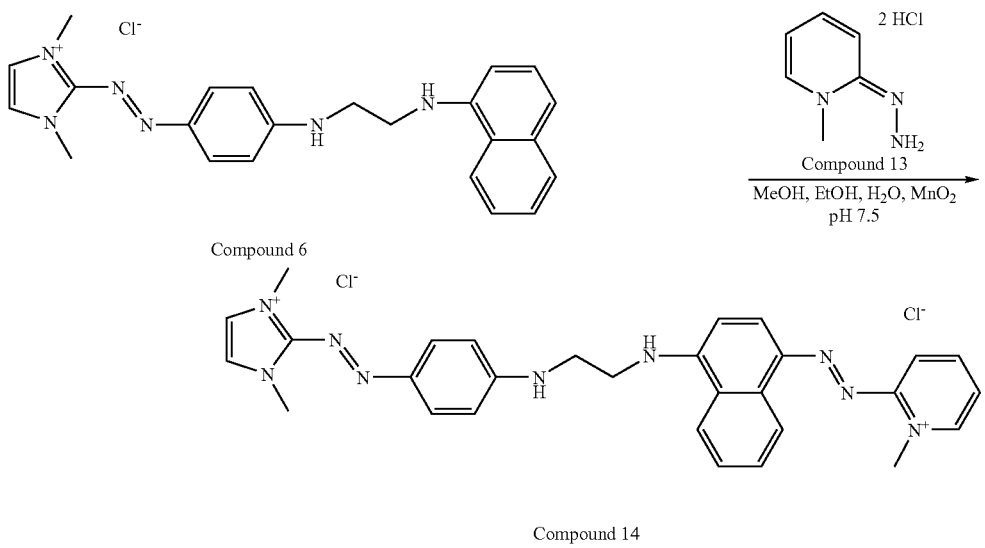

Compound 14

1-methylpyridin-2(1H)-one hydrazone [13] can be obtained using the reference: Hünig, Liebigs Ann. Chem., 617, 1958, 180-202.

[13] (0.196 g; 1 mmole) and [6] (0.420 g; 1 mmole) were dissolved in methanol (5 ml), ethanol (15 ml) and water (5 ml). The pH was adjusted to 7 by addition of 3% aqueous sodium hydroxide.

Manganese dioxide (0.870 g; 10 mmoles) was added slowly to the reaction mixture adjusting the pH to 7.5 by dropwise addition of 1N aqueous hydrochloride. The reaction mixture was stirred at room temperature for 12 hours.

The reaction mixture was beforehand filtered to remove manganese salts. 50 ml of acetone was added to the reaction mixture.

A precipitate formed, was filtered off, rinsed with isopropanol, and ethyl acetate and dried over $P_2O_5$ under vacuum overnight to give a black powder of [14].

Standard analytical characterization was in agreement with the structure.

Example 5 of Dyeing:
The following composition was prepared:

| Ingredients | Amount |
|---|---|
| Alkyl (C8/C10 50/50) polyglucoside (2) (60% buffered aqueous solution) | 12 g |
| Ethanol | 20 g |
| Benzyl alcohol | 4 g |
| Polyethyleneglycol 400 (8 EO) | 6 g |
| water | qsp 100 g |

$5 \times 10^{-3}$ mol/l of the compound prepared before was solubilized into the above composition.

The resulting mixture was applied onto locks of hair with 90% of white hair, at ambient temperature, for a period of 30 minutes.

The locks of hair were then rinsed, washed with a standard shampoo, rinsed again and dried.

The hair was dyed in a dull grey shade which was resistant to shampooing.

Example 6

Synthesis of the Compound [18]:

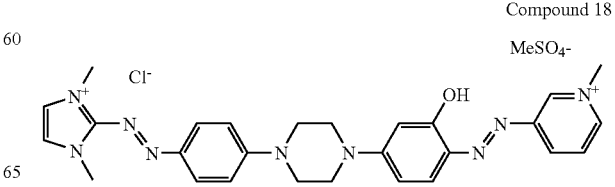

Compound 18

Synthetic Route

Step 1:

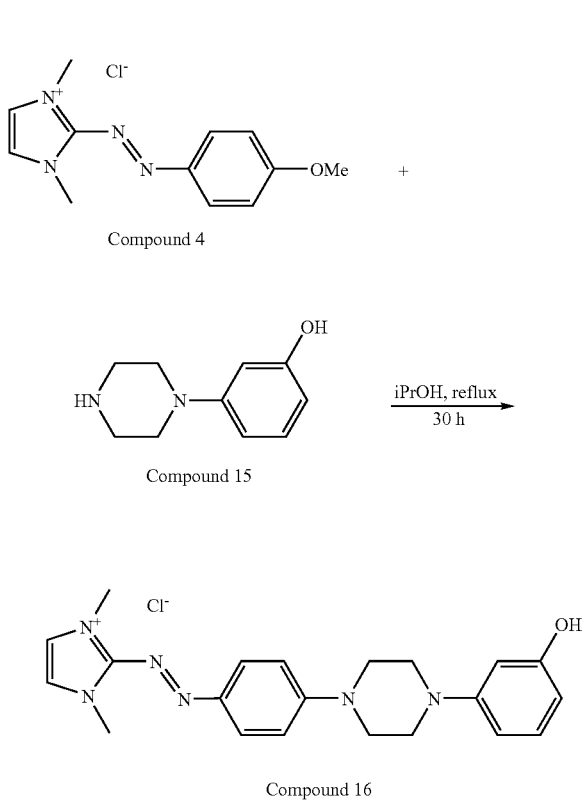

3-piperazin-1-yl phenol [15] is commercially available.

A mixture of [4] (67.95 g; 255 mmol) and [15] (50 g; 281 mmol) in 650 ml 2-propanol was heated 30 h to reflux. The mixture was cooled to room temperature and filtered.

The solid was washed with 2-propanol (1 L). After drying in vacuo, 74.2 g (71%) of a dark red solid were obtained. The solid was suspended in 1 L of water containing 50 mL of 1 M aqueous HCl, filtered, and the residue suspended in 500 mL refluxing 2-propanol.

The suspension was filtered hot and washed with warm 2-propanol. The filter cake was dried in vacuo yielding 59.1 g (56%) of a dark red solid of [16].

Step 2:

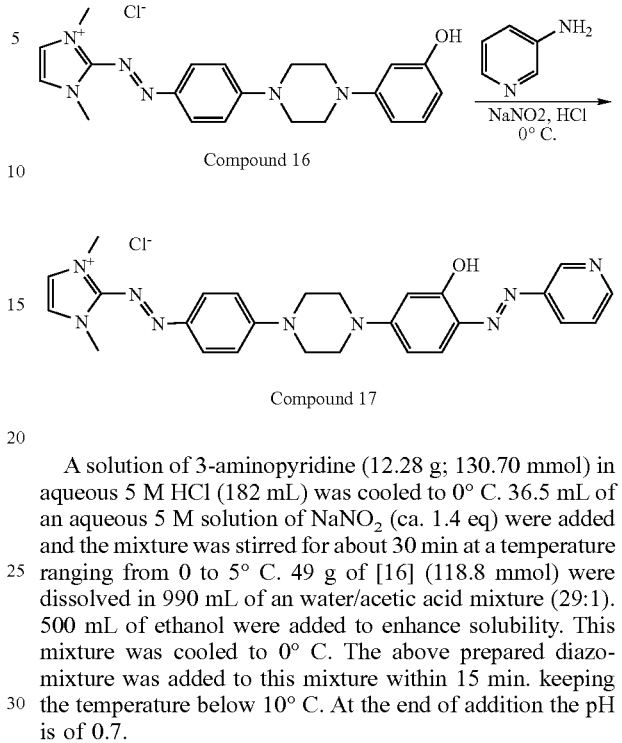

A solution of 3-aminopyridine (12.28 g; 130.70 mmol) in aqueous 5 M HCl (182 mL) was cooled to 0° C. 36.5 mL of an aqueous 5 M solution of $NaNO_2$ (ca. 1.4 eq) were added and the mixture was stirred for about 30 min at a temperature ranging from 0 to 5° C. 49 g of [16] (118.8 mmol) were dissolved in 990 mL of an water/acetic acid mixture (29:1). 500 mL of ethanol were added to enhance solubility. This mixture was cooled to 0° C. The above prepared diazo-mixture was added to this mixture within 15 min. keeping the temperature below 10° C. At the end of addition the pH is of 0.7.

The red-brownish suspension was set to a pH of 4.5 by addition of an aqueous 10 M NaOH solution. This mixture was allowed to slowly warm to room temperature keeping the pH at 4.5 by adding further amounts of NaOH solution.

The red suspension was filtered and the filter cake washed with 1.5 L of an acidic water/ethanol-mixture (2:1; pH=4 by addition of 4 mL 1 M HCl).

The solid was then solubilized in refluxing water (500 mL). The oil bath was removed and at 60° C., 50 mL of acetone were added and the mixture allowed to cool down to room temperature. A very fine solid precipitated that was filtered.

This solid was suspended in hot acetone (500 mL), filtered hot, and washed with acetone. The residue was dried under vaccuum 20° C. to yield 35.6 g (58%) of a dark-red solid [17].

Step 3:

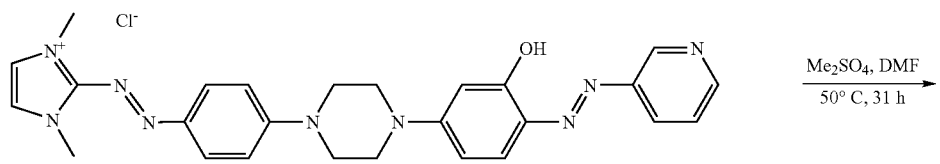

Compound 17

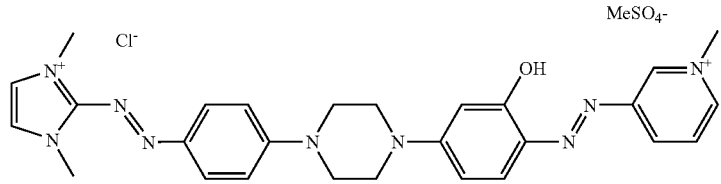

Compound 18

A solution of [17] (283 mg; 0.547 mmol) and 0.602 mmol (1.1 equiv) of dimethyl sulphate in 2.5 mL N,N-dimethylformamide was heated to 50° C. for 24 h. To obtain full conversion, a further 0.602 mmol of dimethyl sulphate was added and the mixture heated another 7 h at 50° C. The mixture was cooled to room temperature and evaporated.

The crude residue was taken in 2-propanol (5 mL) and heated to reflux for 15 min.

The suspension was filtered hot and washed with warm 2-propanol. The residue solid was dried under vacuum to yield 191 mg (54%) of a dark red solid [18].

Example 6 of Dyeing:

The following composition was prepared:

| Ingredients | Amount |
| --- | --- |
| Alkyl (C8/C10 50/50) polyglucoside (2) (60% buffered aqueous solution) | 12 g |
| Ethanol | 20 g |
| Benzyl alcohol | 4 g |

-continued

| Ingredients | Amount |
| --- | --- |
| Polyethyleneglycol 400 (8 EO) | 6 g |
| water | qsp 100 g |

$5 \times 10^{-3}$ mol/l of the compound prepared before was solubilized into the above composition.

The resulting mixture was applied onto locks of hair with 90% of white hair, at ambient temperature during 30 minutes.

The locks of hair were then rinsed, washed with a standard shampoo, rinsed again and dried.

The hair was dyed in a red shade which was resistant to shampooing.

Example 7

Synthesis of the Compound [19]:

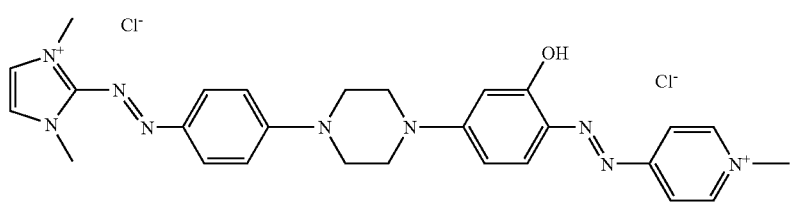

Compound 19

Synthetic Route

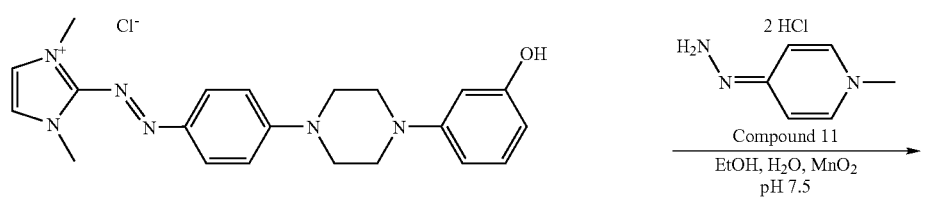

Compound 16

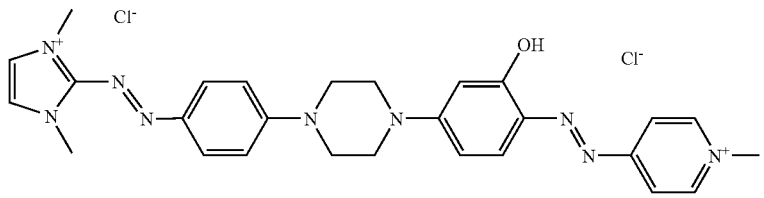

Compound 19

[11] (0.196 g; 1 mmole) and [16] (0.412 g; 1 mmole) were dissolved in ethanol (5 ml) and water (10 ml). The pH was adjusted to 7 by addition of 3% aqueous sodium hydroxide.

Manganese dioxide (0.870 g; 10 mmoles) was added slowly to the reaction mixture adjusting the pH to 7-7.5 by addition of 1N aqueous hydrochloride. The reaction mixture was stirred at room temperature for 12 hours.

The reaction mixture was beforehand filtered to remove manganese salts. 50 ml of acetone was added to the reaction mixture.

A precipitate formed, was filtered off, rinsed with isopropanol, and ethyl acetate and dried over $P_2O_5$ under vacuum overnight to give a dark red powder of [19].

Standard analytical characterization was in agreement with the structure.

Example 7 of Dyeing:

The following composition was prepared:

| Ingredients | Amount |
| --- | --- |
| Alkyl (C8/C10 50/50) polyglucoside (2) (60% buffered aqueous solution) | 12 g |
| Ethanol | 20 g |
| Benzyl alcohol | 4 g |
| Polyethyleneglycol 400 (8 EO) | 6 g |
| water | qsp 100 g |

$5 \times 10^{-3}$ mol/l of the compound prepared before was solubilized into the above composition.

The resulting mixture was applied onto locks of hair with 90% of white hair, at ambient temperature, for a period of 30 minutes.

The locks of hair were then rinsed, washed with a standard shampoo, rinsed again and dried.

The hair was dyed in a fuchsia shade which was resistant to shampooing.

Example 8

Synthesis of the Compound [20]:

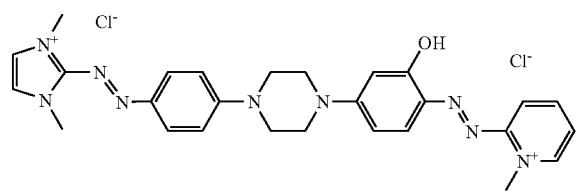

Compound 20

Synthetic Route

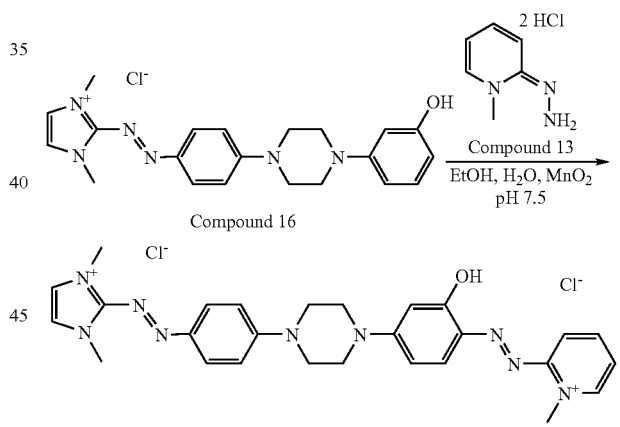

Compound 20

[13] (0.196 g; 1 mmole) and [16] (0.412 g; 1 mmole) were dissolved in ethanol (5 ml) and water (10 ml). The pH was adjusted to 7 by addition of 3% aqueous sodium hydroxide.

Manganese dioxide (0.870 g; 10 mmoles) was added slowly to the reaction mixture adjusting the pH to 7.5 by addition of 1N aqueous hydrochloride. The reaction mixture was stirred at room temperature for 12 hours.

The reaction mixture was beforehand filtered to remove manganese salts. 50 ml of acetone was added to the reaction mixture.

A precipitate formed, was filtered off, rinsed with isopropanol, and ethyl acetate and dried over $P_2O_5$ under vacuum overnight to give a dark red powder of [20].

Standard analytical characterization was in agreement with the structure.

Example 8 of Dyeing:

The following composition was prepared:

| Ingredients | Amount |
|---|---|
| Alkyl (C8/C10 50/50) polyglucoside (2) (60% buffered aqueous solution) | 12 g |
| Ethanol | 20 g |
| Benzyl alcohol | 4 g |
| Polyethyleneglycol 400 (8 EO) | 6 g |
| water | qsp 100 g |

$5 \times 10^{-3}$ mol/l if the compound prepared before was solubilized into the above composition.

The resulting mixture was applied onto locks of hair with 90% of white hair, at ambient temperature, for a period of 30 minutes.

The locks of hair were then rinsed, washed with a standard shampoo, rinsed again and dried.

The hair was dyed in a fuchsia shade which was resistant to shampooing

What is claimed is:

1. A cationic diazo compound chosen from those of formula (I) and the acid addition salts thereof:

in which:

Dye1 and Dye2 are such that the compound of formula (I) is not symmetrical, and are chosen from:

Dye 1:

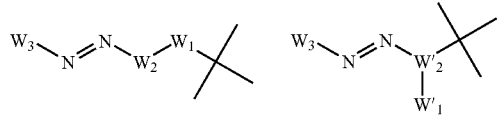

Dye 2:

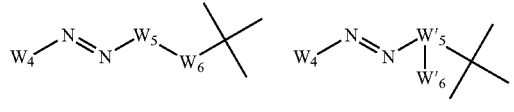

wherein:

$W_1$ and $W_6$, independently of each other, are chosen from —$NR_1$— groups and —O— atoms, in which $R_1$ is chosen from a hydrogen atom and saturated and unsaturated, aromatic and non-aromatic, optionally substituted $C_1$-$C_{20}$ hydrocarbon-based chains, which can form at least one optionally substituted 3- to 7-membered carbon-based rings, optionally interrupted with at least one hetero atom or with at least one group bearing at least one hetero atom;

$W'_1$ and $W'_6$, independently of each other, are chosen from —$NR'_1R'_2$ and —$OR'_3$ groups, in which $R'_1$, $R'_2$ and $R'_3$, independently of each other, are chosen from hydrogen atoms and saturated and unsaturated, aromatic and non-aromatic, optionally substituted $C_1$-$C_{20}$ hydrocarbon-based chains, which can form at least one optionally substituted 3- to 7-membered carbon-based ring, optionally interrupted with at least one hetero atom or with at least one group bearing at least one hetero atom; $R'_1$ and $R'_2$ possibly forming, with the nitrogen atom to which they are attached, an optionally substituted 5- or 7-membered heterocycle optionally comprising another nitrogen or non-nitrogen hetero atom;

the radicals $R_1$ of $W_1$ and $W_6$, together or separately, may form with all or part of the group LK and with the nitrogen atom to which each is attached a saturated or unsaturated, aromatic or non-aromatic, optionally substituted 5- to 7-membered heterocycle;

the radicals $R'_1$, $R'_2$ or $R'_3$ of $W'_1$ and $W'_6$, together or separately, may form, with all or part of the group LK and with the nitrogen or oxygen atom to which each is attached, a saturated or unsaturated, aromatic or non-aromatic, optionally substituted 5- to 7-membered heterocycle;

$W_2$, $W_5$, $W'_2$ and $W'_5$, independently of each other, are chosen from groups of formulae (a), (b), and (c):

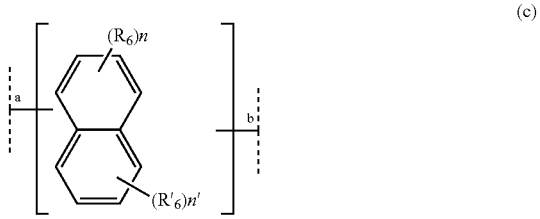

in which formulae:

$X_1$ is chosen from a nitrogen atom and a group $CR_7$;

$X_2$ is chosen from a nitrogen atom and a group $CR_8$;

$Z_1$ is chosen from a nitrogen atom and a group $CR_{10}$;

$Z_2$ is chosen from a nitrogen atom and a group $CR_{11}$;

$R_4$, $R_5$, $R_6$, $R'_6$, $R_7$, $R_8$, $R_{10}$ and $R_{11}$, independently of each other, are chosen from:

linear and branched, saturated and unsaturated, aromatic and non-aromatic, optionally substituted $C_1$-$C_{16}$ hydrocarbon-based chains, which can form at least one optionally substituted 3- to 7-membered carbon-based ring, optionally interrupted with at least one hetero atom or with at least one group bearing at least one hetero atom;

hydroxyl groups, $C_1$-$C_4$ alkoxy groups, $C_2$-$C_4$ (poly)hydroxyalkoxy groups;

alkoxycarbonyl groups (RO—CO—) in which R is chosen from $C_1$-$C_4$ alkyl radicals, alkylcarbonyloxy radicals (RCO—O—) in which R is chosen from $C_1$-$C_4$ alkyl radicals;

amino groups, amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;

alkylcarbonylamino groups (RCO—NR—) in which the radicals R, independently of each other, are chosen from $C_1$-$C_4$ alkyl radicals;

carbamoyl groups $((R)_2N—CO)$ in which the radicals R, independently of each other, are chosen from hydrogen atoms and $C_1$-$C_4$ alkyl radicals;

ureido groups $(N(R)_2—CO—NR'—)$ in which the radicals R and R', independently of each other, are chosen from hydrogen atoms and $C_1$-$C_4$ alkyl radicals;

sulfonamide groups $((R)_2N—SO_2—)$ in which the radicals R, independently of each other, are chosen from hydrogen atoms and $C_1$-$C_4$ alkyl radicals;

alkylsulfonylamino groups $(RSO_2—NR'—)$ in which the radicals R and R', independently of each other, are chosen from hydrogen atoms and $C_1$-$C_4$ alkyl radicals;

guanidinium groups $((R')_2N—C(=NH_2^+)—NR—)$ in which the radicals R and R', independently of each other, are chosen from hydrogen atoms and $C_1$-$C_4$ alkyl radicals;

nitro groups;

cyano groups; and halogen atoms;

wherein $R_4$, $R_5$, $R_7$, $R_8$, $R_{10}$ and $R_{11}$ may each be a hydrogen atom;

wherein $R_4$, $R_5$, $R_6$, $R'_6$, $R_7$, $R_8$, $R_{10}$ and $R_{11}$, independently of each other, may form, with, all or some of the groups $W'_1$ or $W'_6$, or alternatively, all or some of the groups $W_1$ or $W_6$, a saturated or unsaturated, aromatic or non-aromatic, optionally substituted 5- to 7-membered heterocycle;

a bond from $W'_2$ to $W'_1$ or to the group LK, or from $W'_5$ to $W'_6$ or to the group LK;

a is the bond from $W_2$, $W_5$, $W'_2$ or $W'_5$ to the azo group —N=N—;

b is the bond from $W_2$ to $W_1$, from $W_5$ to $W_6$, from $W'_2$ to $W'_1$ or to the group LK, or from $W'_5$ to $W'_6$ or to the group LK;

$R_9$ is chosen from:
a hydrogen atom,
linear and branched, saturated and unsaturated, aromatic and non-aromatic, optionally substituted $C_1$-$C_{16}$ hydrocarbon-based chains, which can form at least one optionally substituted 3- to 7-membered carbon-based ring, n and n' are integers and the sum of n and n' is less than or equal to 6;

$W_3$ and $W_4$, independently of each other, are cationic heteroaromatic radicals chosen from those of formulae (1) to (11):

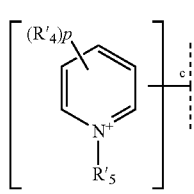
(1)

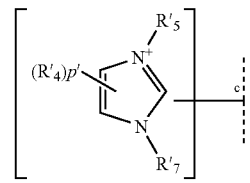
(2)

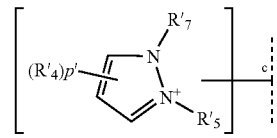
(3)

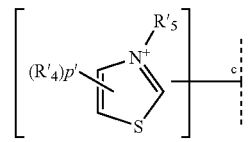
(4)

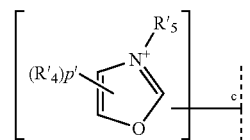
(5)

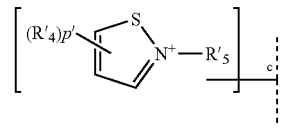
(6)

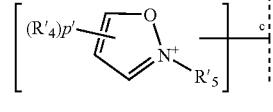
(7)

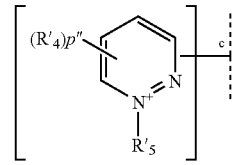
(8)

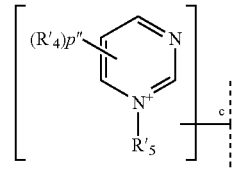
(9)

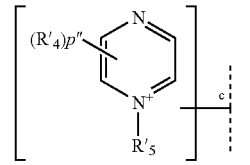
(10)

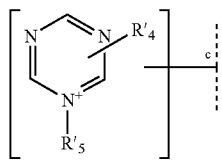

(11)

in which:

R'$_4$, which may be identical or different, substituting the main ring, is chosen from:
- linear and branched, saturated and unsaturated, aromatic and non-aromatic, optionally substituted C$_1$-C$_{16}$ hydrocarbon-based chains, which can form at least one 3- to 6-membered carbon-based ring, optionally interrupted with at least one hetero atom or with at least one group bearing at least one hetero atom;
- hydroxyl groups,
- C$_1$-C$_4$ alkoxy groups,
- C$_2$-C$_4$ (poly)hydroxyalkoxy groups;
- alkoxycarbonyl groups (RO—CO—) in which R is chosen from C$_1$-C$_4$ alkyl radicals,
- alkylcarbonyloxy radicals (RCO—O—) in which R is a C$_1$-C$_4$ alkyl radical;
- amino groups,
- amino groups substituted with at least one C$_1$-C$_4$ alkyl radicals, independently of each other, optionally bearing at least one hydroxyl group, the two alkyl radicals possibly forming, with the nitrogen atom to which they are attached, a 5- or 6-membered heterocycle optionally bearing another nitrogen or non-nitrogen hetero atom;
- alkylcarbonylamino groups (RCO—NR'—) in which the radical R is a C$_1$-C$_4$ alkyl radical and the radical R' is chosen from hydrogen and C$_1$-C$_4$ alkyl radicals;
- carbamoyl groups ((R)$_2$N—CO—) in which the radicals R are chosen from, independently of each other, hydrogen atoms or C$_1$-C$_4$ alkyl radicals;
- ureido groups (N(R)$_2$—CO—NR'—) in which the radicals R and R', independently of each other, are chosen from hydrogen atoms and C$_1$-C$_4$ alkyl radicals;
- sulfonamide groups ((R)$_2$N—SO$_2$—) in which the radicals R, independently of each other, are chosen from hydrogen atoms and C$_1$-C$_4$ alkyl radicals;
- alkylsulfonylamino groups (RSO$_2$—NR'—) in which the radicals R and R', independently of each other, are chosen from hydrogen atoms and C$_1$-C$_4$ alkyl radicals;
- guanidinium groups ((R')$_2$N—C(=NH$_2^+$)—NR—) in which the radicals R and R', independently of each other, are chosen from hydrogen atoms and C$_1$-C$_4$ alkyl radicals;
- nitro groups;
- cyano groups; and
- halogen atoms;

wherein two radicals R'$_4$ borne by two adjacent carbon atoms of the main ring may optionally form an aromatic or non-aromatic, 5- or 6-membered secondary ring, optionally substituted with at least one entity chosen from hydrogen, hydroxyl groups, C$_1$-C$_4$ alkyl radicals, C$_1$-C$_4$ alkoxy radicals, C$_2$-C$_4$(poly)hydroxyalkoxy radicals, amino radicals, amino radicals substituted with at least one C$_1$-C$_4$ alkyl radical, which may be identical or different, optionally bearing at least one hydroxyl group;

R'$_5$, borne by the quaternized nitrogen atom, is chosen from linear and branched, saturated and unsaturated, aromatic and non-aromatic, optionally substituted C$_1$-C$_{16}$ hydrocarbon-based chains, which can form an optionally substituted 3- to 7-membered carbon-based ring, optionally interrupted with at least one hetero atom or with at least one group bearing at least one hetero atom; the radical R'$_5$ is such that the atom directly linked to the quaternized nitrogen atom is a carbon atom;

R'$_7$ is chosen from optionally substituted C$_1$-C$_4$ alkyl radicals; optionally substituted phenyl radicals; and optionally substituted benzyl radicals;

the bond c links the cationic radical defined by formulae (1) to (11) to the azo group; the bond may be on the main or secondary ring;

p is an integer ranging from 0 to 4, p' is an integer ranging from 0 to 2, and p" is an integer ranging from 0 to 3;

when the main ring does not bear the maximum number of substituents, then the unsubstituted position(s) bear(s) a nitrogen atom; with the condition that at least one of the two groups W$_3$ and W$_4$ are not chosen from unsubstituted imidazolium groups;

LK is chosen from saturated and unsaturated, linear and branched, cyclic and non-cyclic, aromatic and non-aromatic, optionally substituted C$_2$-C$_{40}$ hydrocarbon-based chains, optionally interrupted with at least one hetero atom or group comprising at least one hetero atom, with the proviso that the group LK does not comprise any nitro, nitroso or peroxo groups or bonds wherein the LK does not bear a cationic charge; LK may end with a hetero atom or group bearing at least one hetero atom, if LK is linked to W'$_2$ or W'$_5$; LK may end with a group bearing at least one hetero atom chosen from —CO— and —SO$_2$— if LK is linked to W$_6$ or W$_1$; and wherein the electrical neutrality of the compound is ensured by at least one cosmetically acceptable anions An.

2. The cationic diazo compound according to claim 1, wherein R$_1$, R'$_1$, R'$_2$ and R'$_3$, independently of each other, are chosen from:
- hydrogen atoms;
- optionally substituted C$_1$-C$_6$ alkyl radicals;
- aryl and arylalkyl radicals, the aryl part being optionally substituted;
- wherein the radicals R$_1$ of W$_1$ and W$_6$, together or separately, can form, with all or part of the group LK and with the nitrogen atom to which each is attached, a saturated or unsaturated, aromatic or non-aromatic, optionally substituted 5- to 7-membered heterocycle; and
- wherein the radicals R'$_1$, R'$_2$ or R'$_3$ of W'$_1$ and W'$_6$, together or separately, can form, with all or part of the group LK and with the nitrogen or oxygen atom to which each is attached, a saturated or unsaturated, aromatic or non-aromatic, optionally substituted 5- to 7-membered heterocycle.

3. The cationic diazo compound according to claim 1, wherein the radicals $R_1$, $R'_1$, $R'_2$ and $R'_3$, which may be identical or different, are chosen from:
hydrogen atoms;
optionally substituted $C_1$-$C_3$ alkyl radicals;
phenyl radicals, optionally substituted with at least one radical chosen from hydroxyl, $C_1$-$C_2$ alkoxy, and amino radicals, or amino radicals substituted with at least one $C_1$-$C_4$ group optionally bearing at least one hydroxyl group;
wherein the radicals $R_1$ of $W_1$ and $W_6$, or alternatively, the radicals $R'_1$, $R'_2$ and $R'_3$ of $W'_1$ and $W'_6$, can form, with the nitrogen or oxygen atom for $R'_3$ to which each is attached and all or part of the group LK, a 5- to 7-membered heterocycle of pyrrolidine, piperidine, piperazine or homopiperazine type optionally substituted with at least one methyl, hydroxyl, amino or (di)methylamino radical.

4. The cationic diazo compound according to claim 1, wherein $R_1$, $R'_1$, $R'_2$ and $R'_3$, which may be identical or different, are chosen from:
hydrogen atoms;
methyl, ethyl and 2-hydroxyethyl radicals;
phenyl radicals, optionally substituted with a hydroxyl, methoxy, amino, (di)methylamino or (di)(2-hydroxyethyl)amino radical;
wherein the radicals $R_1$ of $W_1$ and $W_6$, or alternatively, the radicals $R'_1$, $R'_2$ and $R'_3$ of $W'_1$ and $W'_6$, on the other hand, can form, with the nitrogen or oxygen atom for $R'_3$ to which each is attached and all or part of the group LK, a 5- to 7-membered heterocycle such as pyrrolidine, 3-hydroxypyrrolidine, 3-dimethylaminopyrrolidine, piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine or 1-methyl-1,4-perhydrodiazepine.

5. The cationic diazo compounds according to claim 1, wherein the radicals $R_4$, $R_5$, $R_6$, $R'_6$, $R_7$, $R_8$, $R_9$, $R_{10}$ and $R_{11}$, which may be identical or different, are chosen from:
hydrogen atoms for $R_4$, $R_5$, $R_7$, $R_8$, $R_{10}$ and $R_{11}$;
optionally substituted $C_1$-$C_{16}$ alkyl radicals;
halogen atoms;
hydroxyl groups;
$C_1$-$C_2$ alkoxy radicals;
$C_2$-$C_4$ (poly)hydroxyalkoxy radicals;
amino radicals;
amino radicals substituted with one or two $C_1$-$C_4$-alkyl radicals, which may be identical or different, optionally bearing at least one hydroxyl or $C_1$-$C_4$ dialkylamino group;
alkylcarbonylamino radicals (RCO—NR'—) in which the radical R is chosen from $C_1$-$C_4$ alkyl radicals and the radical R' is chosen from hydrogen atoms and $C_1$-$C_4$ alkyl radicals;
carbamoyl radicals ($(R)_2$N—CO—) in which the radicals R, which may be identical or different, are chosen from hydrogen atoms and $C_1$-$C_4$ alkyl radicals optionally bearing at least one hydroxyl group;
alkylsulfonylamino radicals (R'SO$_2$—NR—) in which the radical R is chosen from hydrogen atoms and $C_1$-$C_4$ alkyl radicals optionally bearing at least one hydroxyl group, the radical R' is chosen from $C_1$-$C_4$ alkyl radicals;
aminosulfonyl radicals ($(R)_2$N—SO$_2$—) in which the radicals R, which may be identical or different, are chosen from hydrogen atoms and $C_1$-$C_4$ alkyl radicals optionally bearing at least one hydroxyl group; and
a bond from $W'_2$ to $W'_1$ or to the group LK, or from $W'_5$ to $W'_6$ or to the group LK.

6. The cationic diazo compound according to claim 1, wherein the radicals $R_4$, $R_5$, $R_6$, $R'_6$, $R_7$, $R_8$, $R_{10}$ and $R_{11}$, which may be identical or different, are chosen from:
hydrogen atoms for $R_4$, $R_5$, $R_7$, $R_8$, $R_{10}$ and $R_{11}$;
$C_1$-$C_4$ alkyl radicals optionally substituted with at least one radical chosen from hydroxyl and acylamino radicals, or amino radicals substituted with two identical or different $C_1$-$C_2$ alkyl radicals, optionally bearing at least one hydroxyl group, or a $C_1$-$C_2$ alkoxy radical;
amino radicals; amino radicals substituted with one or two identical or different $C_1$-$C_2$ alkyl radicals, optionally bearing at least one hydroxyl group; acylamino radicals; carbamoyl radicals; sulfonylamino radicals;
hydroxyl radicals; $C_1$-$C_2$ alkoxy radicals; and
a bond from $W'_2$ to $W'_1$ or to the group LK, or from $W'_5$ to $W'_6$ or to the group LK.

7. The cationic diazo compound according to claim 1, wherein the radical $R_9$ is chosen from a hydrogen atom, $C_1$-$C_{15}$ alkyl radicals; $C_2$-$C_6$ monohydroxyalkyl radicals; $C_2$-$C_6$-polyhydroxyalkyl radicals; ($C_1$-$C_6$)alkoxy($C_2$-$C_6$) alkyl radicals; optionally substituted aryl radicals; optionally substituted arylalkyl radicals; $C_2$-$C_6$ amidoalkyl radicals; $C_2$-$C_6$ aminoalkyl radicals, the amine of which is substituted with two identical or different, optionally substituted $C_1$-$C_4$ alkyl radicals.

8. The cationic diazo compound according to claim 1, wherein the radical $R_9$ is chosen from a hydrogen atom, $C_1$-$C_6$ alkyl radicals, $C_2$-$C_6$ monohydroxyalkyl radicals; $C_2$-$C_6$ polyhydroxyalkyl radicals; ($C_1$-$C_6$)alkoxy($C_2$-$C_6$) alkyl radicals; phenyl radicals optionally substituted with at least one entity chosen from chlorine atoms, hydroxyl groups, and RCO—NH— groups in which R is chosen from $C_1$-$C_4$ alkyl radicals or amino radicals substituted with two identical or different $C_1$-$C_4$ alkyl radicals; benzyl radicals; $C_1$-$C_6$ aminoalkyl radicals; $C_1$-$C_6$ aminoalkyl radicals in which the amine is substituted with two identical or different $C_1$-$C_4$ alkyl radicals.

9. The cationic diazo compound according to claim 1, wherein $W_2$, $W_5$, $W'_2$ and $W'_5$, which may be identical or different, are chosen from the compounds of formula (a) or (c).

10. The cationic compound according to claim 1, wherein $X_1$ is a group $CR_7$.

11. The cationic diazo compound according to claim 10, wherein $X_2$ is a group $CR_8$.

12. The cationic diazo compound according to claim 1, wherein $W_3$ and $W_4$, independently of each other, are aromatic heterocycles chosen from those of formulae (1), (2), and (3):

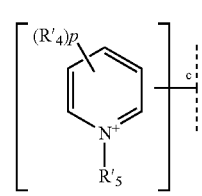

(1)

-continued

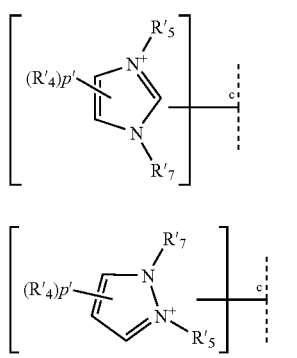

in which $R'_4$, $R'_5$, $R'_7$, p, p' and c are defined in claim 1.

13. The cationic diazo compound according to claim 12, wherein the aromatic heterocycle is chosen from 2-imidazolium, 2-benzimidazolium, 2-pyridinium, 3-pyridinium, 4-pyridinium, 2-quinolinium, 4-quinolinium, 3-pyrazolium, 4-pyrazolium, 3-indazolium, 4-indazolium, 5-indazolium, 6-indazolium and 7-indazolium; on the condition that at least one of the two groups $W_3$ or $W_4$ is not an unsubstituted imidazolium group.

14. The cationic diazo compound according to claim 1, wherein LK is chosen from linear, branched and cyclic, aromatic and non-aromatic $C_2$-$C_{20}$ alkyl chains:

optionally interrupted with at least one hetero atom and/or group comprising at least one hetero atom, or with a 5- or 6-membered heterocycle, comprising at least one nitrogen atom; with the proviso that there are no nitro, nitroso or peroxo groups or bonds in the group LK;

optionally ending with a hetero atom or group bearing at least one hetero atom, if LK is linked to $W'_2$ or $W'_5$;

optionally ending with a group bearing at least one hetero atom chosen from —CO— and —$SO_2$— if LK is linked to $W_6$ or $W_1$;

optionally substituted with at least one radical chosen from hydroxyl, $C_1$-$C_2$ alkoxy, $C_2$-$C_4$ (poly)hydroxyalkoxy, amino substituted with at least one linear or branched $C_1$-$C_2$ alkyl group optionally bearing at least one hydroxyl group.

15. The cationic diazo compound according to claim 14, wherein LK is chosen from linear and branched $C_2$-$C_{20}$ alkyl chains, optionally substituted with hydroxyl groups, amino groups substituted with at least one linear or branched $C_1$-$C_4$ alkyl group optionally bearing at least one hydroxyl group; wherein, when LK is linked to $W'_2$ or $W'_5$, LK may optionally end with at least one hetero atom or group comprising at least one hetero atom.

16. The cationic diazo compound according to claim 1, chosen from the following formulae or the acid addition salts thereof:

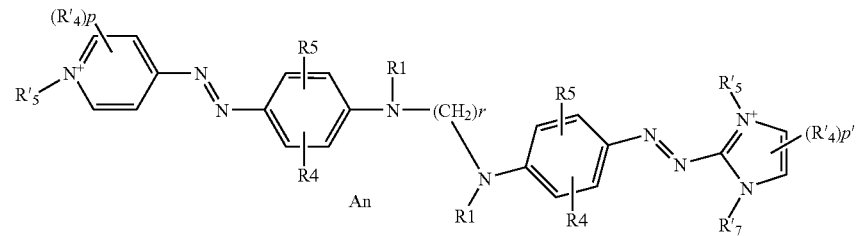

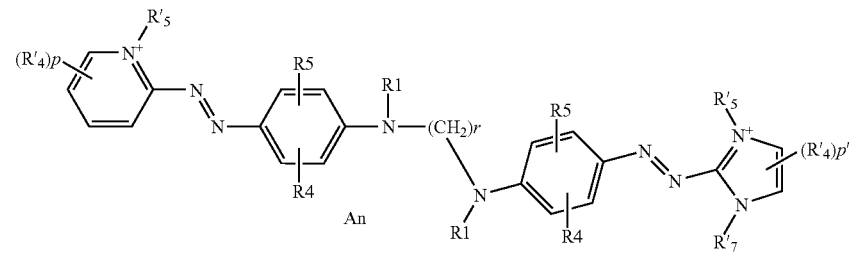

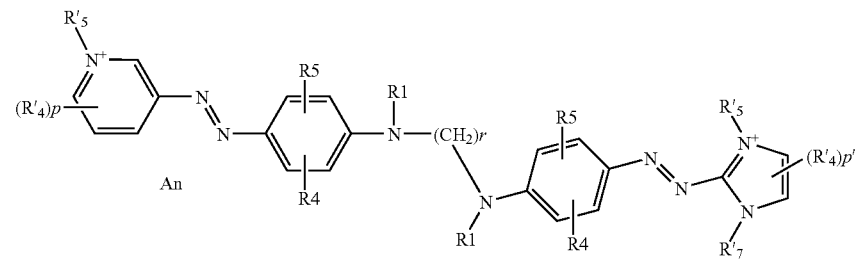

-continued
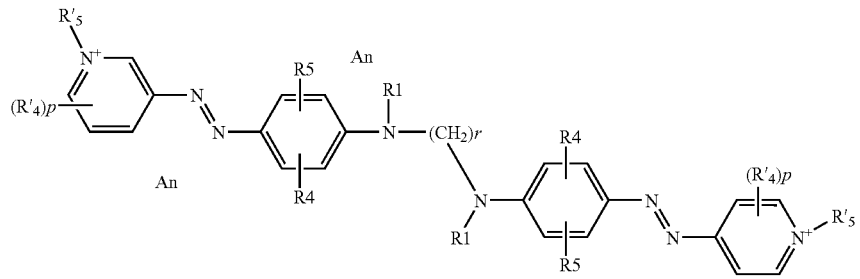
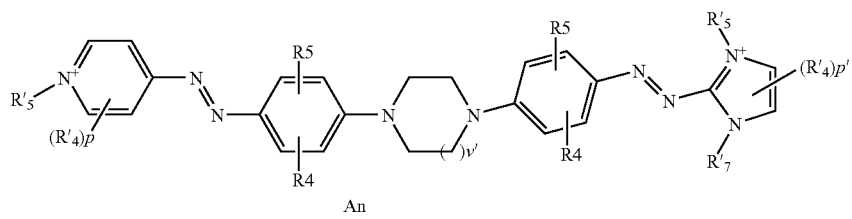
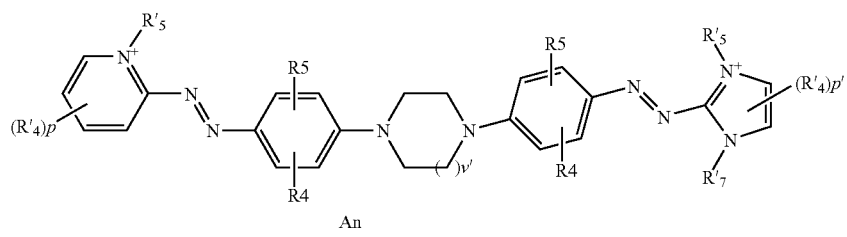
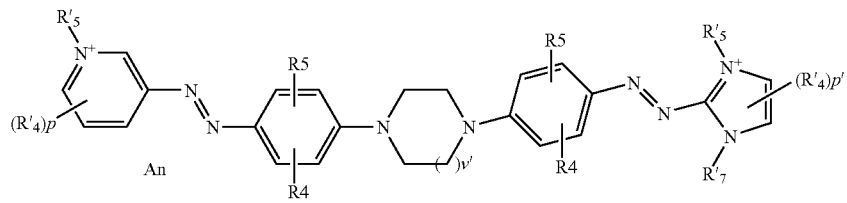
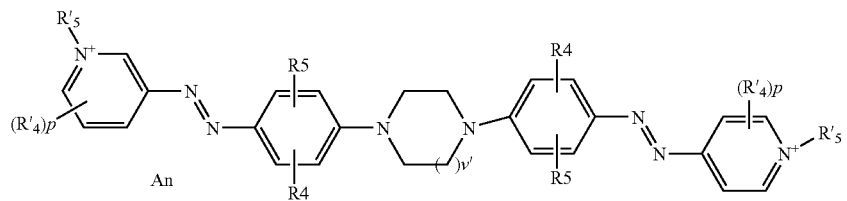
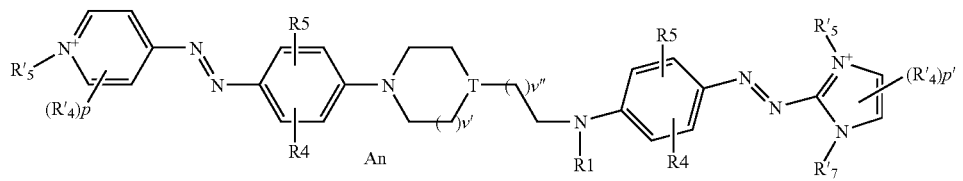
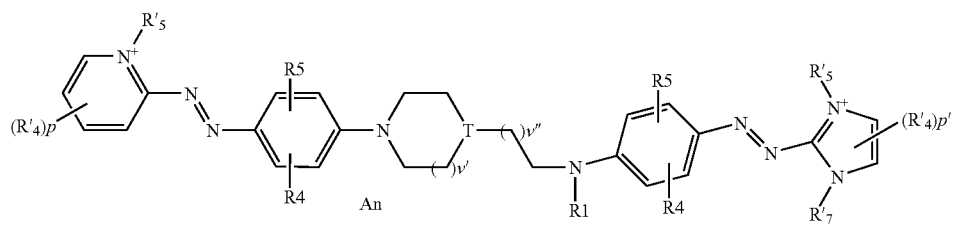

-continued

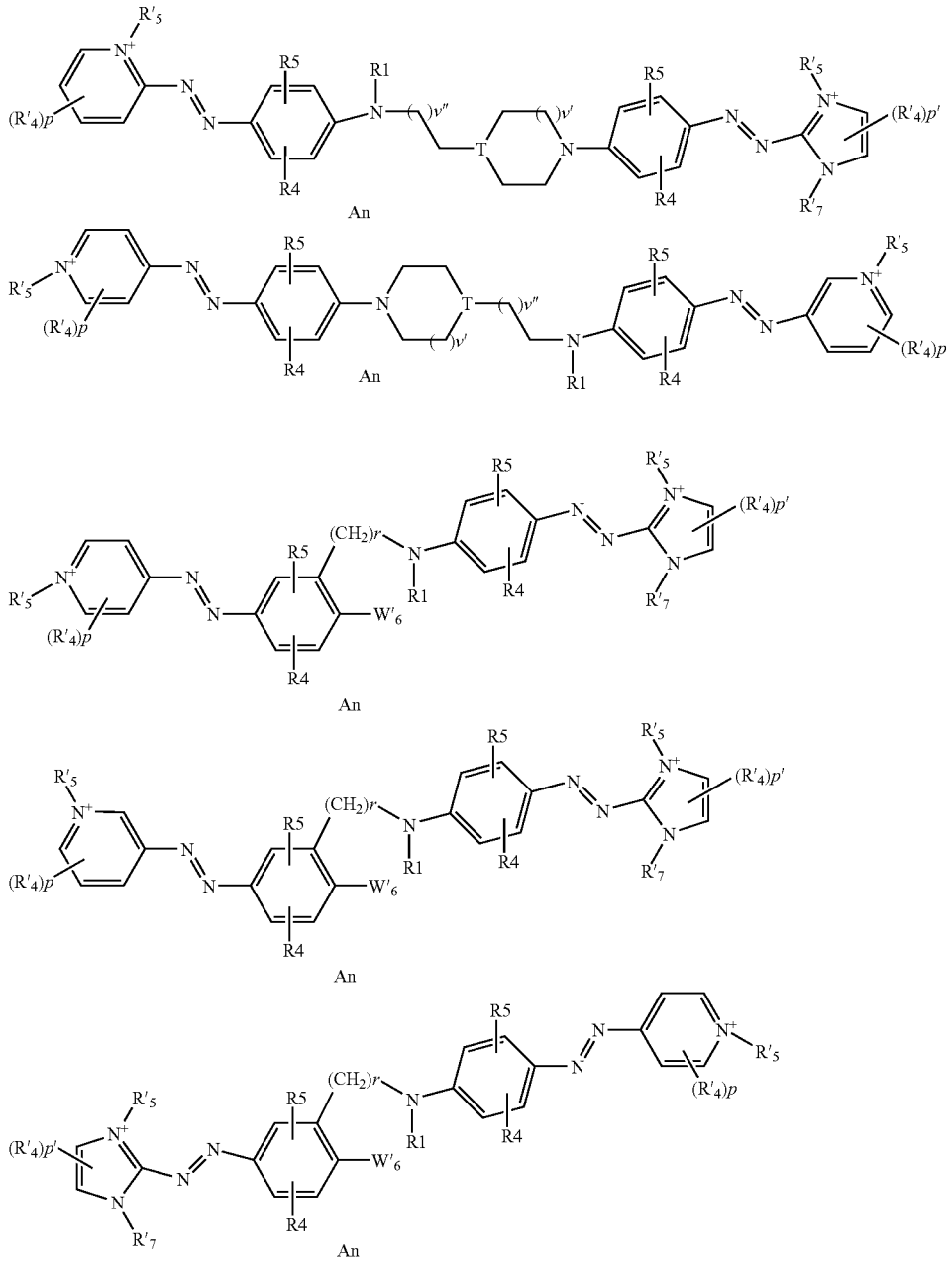

in which formulae $R_1$, $R_4$, $R_5$, $R'_4$, $R'_5$, $R'_7$, $W'_6$, p and p', which may be identical/or different, have the same definitions as in claim 1;

r is an integer ranging from 1 to 10;

v' is an integer equal to 1 or 2

T is a carbon atom or a nitrogen atom v" is an integer equal to 1, 2 or 3; and wherein the electrical neutrality of the molecule is respected by the presence of at least one cosmetically acceptable anions An.

17. The cationic diazo compound according to claim 1, wherein the at least one cosmetically acceptable anion An is chosen from halides; hydroxides; sulfates; hydrogen sulfates; carbonates, hydrogen carbonates; perchlorates; carboxylic acid salts; citrates; tartrates; alkyl sulfates for which the linear or branched alkyl portion is of $C_1$-$C_6$; alkylsulfonates for which the linear or branched alkyl portion is of $C_1$-$C_6$; arylsulfonates for which the aryl portion is optionally substituted with at least one $C_1$-$C_4$ alkyl radicals.

18. A dye composition comprising, in a medium that is suitable for dyeing keratin fibers, at least one direct dye chosen from those of formula (I) and the acid addition salts thereof:

$$\text{Dye1-LK-Dye2} \quad (I)$$

in which:

Dye1 and Dye2 are such that the compound of formula (I) is not symmetrical, and are chosen from:

Dye 1:

Dye 2:

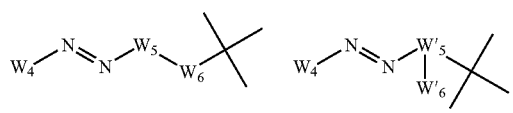

wherein:

$W_1$ and $W_6$, independently of each other, are chosen from —$NR_1$— groups and —O— atoms, in which $R_1$ is chosen from a hydrogen atom and saturated and unsaturated, aromatic and non-aromatic, optionally substituted $C_1$-$C_{20}$ hydrocarbon-based chains, which can form at least one optionally substituted 3- to 7-membered carbon-based rings, optionally interrupted with at least one hetero atom or with at least one group bearing at least one hetero atom;

$W'_1$ and $W'_6$, independently of each other, are chosen from —$NR'_1R'_2$ and —$OR'_3$ groups, in which $R'_1$, $R'_2$ and $R'_3$, independently of each other, are chosen from hydrogen atoms and saturated and unsaturated, aromatic and non-aromatic, optionally substituted $C_1$-$C_{20}$ hydrocarbon-based chains, which can form at least one optionally substituted 3- to 7-membered carbon-based ring, optionally interrupted with at least one hetero atom or with at least one group bearing at least one hetero atom; $R'_1$ and $R'_2$ possibly forming, with the nitrogen atom to which they are attached, an optionally substituted 5- or 7-membered heterocycle optionally comprising another nitrogen or non-nitrogen hetero atom;

the radicals $R_1$ of $W_1$ and $W_6$, together or separately, may form with all or part of the group LK and with the nitrogen atom to which each is attached a saturated or unsaturated, aromatic or non-aromatic, optionally substituted 5- to 7-membered heterocycle;

the radicals $R'_1$, $R'_2$ or $R'_3$ of $W'_1$ and $W'_6$, together or separately, may form, with all or part of the group LK and with the nitrogen or oxygen atom to which each is attached, a saturated or unsaturated, aromatic or non-aromatic, optionally substituted 5- to 7-membered heterocycle;

$W_2$, $W_5$, —$W'_2$ and $W'_5$, independently of each other, are chosen from groups of formulae (a), (b), and (c):

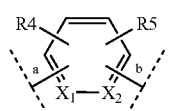

(a)

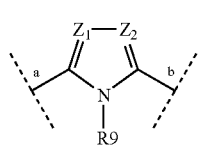

(b)

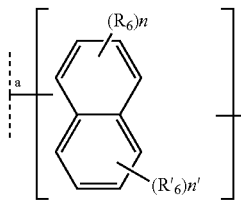

(c)

in which formulae:

$X_1$ is chosen from a nitrogen atom and a group $CR_7$;
$X_2$ is chosen from a nitrogen atom and a group $CR_8$;
$Z_1$ is chosen from a nitrogen atom and a group $CR_{10}$;
$Z_2$ is chosen from a nitrogen atom and a group $CR_{11}$;
$R_4$, $R_5$, $R_6$, $R'_6$, $R_7$, $R_8$, $R_{10}$ and $R_{11}$, independently of each other, are chosen from:
  linear and branched, saturated and unsaturated, aromatic and non-aromatic, optionally substituted $C_1$-$C_{16}$ hydrocarbon-based chains, which can form at least one optionally substituted 3- to 7-membered carbon-based ring, optionally interrupted with at least one hetero atom or with at least one group bearing at least one hetero atom;
  hydroxyl groups,
  $C_1$-$C_4$ alkoxy groups,
  $C_2$-$C_4$ (poly)hydroxyalkoxy groups;
  alkoxycarbonyl groups (RO—CO—) in which R is chosen from $C_1$-$C_4$ alkyl radicals,
  alkylcarbonyloxy radicals (RCO—O—) in which R is chosen from $C_1$-$C_4$ alkyl radicals;
  amino groups,
  amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
  alkylcarbonylamino groups (RCO—NR—) in which the radicals R, independently of each other, are chosen from $C_1$-$C_4$ alkyl radicals;
  carbamoyl groups (($R)_2$N—CO) in which the radicals R, independently of each other, are chosen from hydrogen atoms and $C_1$-$C_4$ alkyl radicals;
  ureido groups (N($R)_2$—CO—NR'—) in which the radicals R and R', independently of each other, are chosen from hydrogen atoms and $C_1$-$C_4$ alkyl radicals;
  sulfonamide groups (($R)_2$N—$SO_2$—) in which the radicals R, independently of each other, are chosen from hydrogen atoms and $C_1$-$C_4$ alkyl radicals;
  alkylsulfonylamino groups ($RSO_2$—NR'—) in which the radicals R and R', independently of each other, are chosen from hydrogen atoms and $C_1$-$C_4$ alkyl radicals;
  guanidinium groups (($R')_2$N—C(=$NH_2^+$)—NR—) in which the radicals R and R', independently of each other, are chosen from hydrogen atoms and $C_1$-$C_4$ alkyl radicals;
  a nitro groups;
  cyano groups; and
  halogen atoms;

wherein $R_4$, $R_5$, $R_7$, $R_8$, $R_{10}$ and $R_{11}$ may each be a hydrogen atom;

wherein $R_4$, $R_5$, $R_6$, $R'_6$, $R_7$, $R_8$, $R_{10}$ and $R_{11}$, independently of each other, may form, with, all or some of the groups $W'_1$ or $W'_6$, or alternatively, all or some of the groups $W_1$ or $W_6$, a saturated or unsaturated, aromatic or non-aromatic, optionally substituted 5- to 7-membered heterocycle;

a bond from $W'_2$ to $W'_1$ or to the group LK, or from $W'_5$ to $W'_6$ or to the group LK;

a is the bond from $W_2$, $W_5$, $W'_2$ or $W'_5$ to the azo group —N=N—;

b is the bond from $W_2$ to $W_1$, from $W_5$ to $W_6$, from $W'_2$ to $W'_1$ or to the group LK, or from $W'_5$ to $W'_6$ or to the group LK;

$R_9$ is chosen from:
  a hydrogen atom,
  linear and branched, saturated and unsaturated, aromatic and non-aromatic, optionally substituted $C_1$-$C_{16}$ hydrocarbon-based chains, which can form at least one optionally substituted 3- to 7-membered carbon-based ring, n and n' are integers and the sum of n and n' is less than or equal to 6;

$W_3$ and $W_4$, independently of each other, are cationic heteroaromatic radicals chosen from those of formulae (1) to (11):

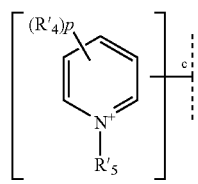
(1)

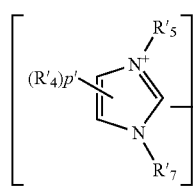
(2)

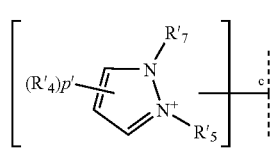
(3)

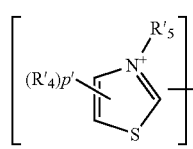
(4)

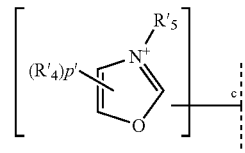
(5)

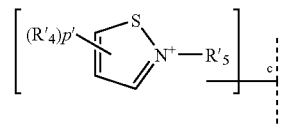
(6)

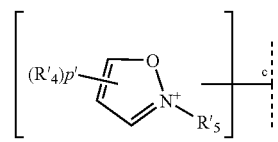
(7)

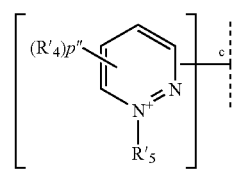
(8)

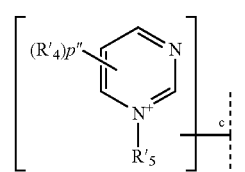
(9)

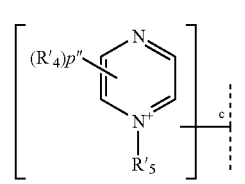
(10)

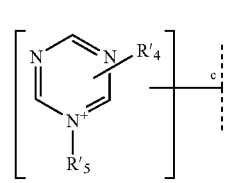
(11)

in which:
$R'_4$ which may be identical or different, substituting the main ring, is chosen from:
  linear and branched, saturated and unsaturated, aromatic and non-aromatic, optionally substituted $C_1$-$C_{16}$ hydrocarbon-based chains, which can form at least one 3- to 6-membered carbon-based ring, optionally interrupted with at least one hetero atom or with at least one group bearing at least one hetero atom;
  hydroxyl groups,
  $C_1$-$C_4$ alkoxy groups,
  $C_2$-$C_4$ (poly)hydroxyalkoxy groups;
  alkoxycarbonyl groups (RO—CO—) in which R is chosen from $C_1$-$C_4$ alkyl radicals,
  alkylcarbonyloxy radicals (RCO—O—) in which R is a $C_1$-$C_4$ alkyl radical;
  amino groups, amino groups substituted with at least one $C_1$-$C_4$ alkyl radicals, independently of each other, optionally bearing at least one hydroxyl group, the two alkyl radicals possibly forming, with the nitrogen atom to which they are attached, a 5- or 6-membered heterocycle optionally bearing another nitrogen or non-nitrogen hetero atom;

alkylcarbonylamino groups (RCO—NR'—) in which the radical R is a $C_1$-$C_4$ alkyl radical and the radical R' is chosen from hydrogen and $C_1$-$C_4$ alkyl radicals;

carbamoyl groups ((R)$_2$N—CO—) in which the radicals R are chosen from, independently of each other, hydrogen atoms or $C_1$-$C_4$ alkyl radicals;

ureido groups (N(R)$_2$—CO—NR'—) in which the radicals R and R', independently of each other, are chosen from hydrogen atoms and $C_1$-$C_4$ alkyl radicals;

sulfonamide groups ((R)$_2$N—SO$_2$—) in which the radicals R, independently of each other, are chosen from hydrogen atoms and $C_1$-$C_4$ alkyl radicals;

alkylsulfonylamino groups (RSO$_2$—NR'—) in which the radicals R and R', independently of each other, are chosen from hydrogen atoms and $C_1$-$C_4$ alkyl radicals;

guanidinium groups ((R')$_2$N—C(=NH$_2^+$)—NR—) in which the radicals R and R', independently of each other, are chosen from hydrogen atoms and $C_1$-$C_4$ alkyl radicals;

nitro groups;

cyano groups; and halogen atoms;

wherein two radicals R'$_4$ borne by two adjacent carbon atoms of the main ring may optionally form an aromatic or non-aromatic, 5- or 6-membered secondary ring, optionally substituted with at least one entity chosen from hydrogen, hydroxyl groups, $C_1$-$C_4$ alkyl radicals, $C_1$-$C_4$ alkoxy radicals, $C_2$-$C_4$(poly)hydroxyalkoxy radicals, amino radicals, amino radicals substituted with at least one $C_1$-$C_4$ alkyl radical, which may be identical or different, optionally bearing at least one hydroxyl group;

R'$_5$, borne by the quaternized nitrogen atom, is chosen from linear and branched, saturated and unsaturated, aromatic and non-aromatic, optionally substituted $C_1$-$C_{16}$ hydrocarbon-based chains, which can form an optionally substituted 3- to 7-membered carbon-based ring, optionally interrupted with at least one hetero atom or with at least one group bearing at least one hetero atom; the radical R'$_5$ is such that the atom directly linked to the quaternized nitrogen atom is a carbon atom;

R'$_7$ is chosen from optionally substituted $C_1$-$C_4$ alkyl radicals; optionally substituted phenyl radicals; and optionally substituted benzyl radicals;

the bond c links the cationic radical defined by formulae (1) to (11) to the azo group; the bond may be on the main or secondary ring;

p is an integer ranging from 0 to 4, p' is an integer ranging from 0 to 2, and p" is an integer ranging from 0 to 3;

when the main ring does not bear the maximum number of substituents, then the unsubstituted position(s) bear(s) a nitrogen atom; with the condition that at least one of the two groups $W_3$ and $W_4$ are not chosen from unsubstituted imidazolium groups;

LK is chosen from saturated and unsaturated, linear and branched, cyclic and non-cyclic, aromatic and non-aromatic, optionally substituted $C_2$-$C_{40}$ hydrocarbon-based chains, optionally interrupted with at least one hetero atom or group comprising at least one hetero atom, with the proviso that the group LK does not comprise any nitro, nitroso or peroxo groups or bonds wherein the LK does not bear a cationic charge; LK may end with a hetero atom or group bearing at least one hetero atom, if LK is linked to W'$_2$ or W'$_5$; LK may end with a group bearing at least one hetero atom chosen from —CO— and —SO$_2$— if LK is linked to $W_6$ or $W_1$; and wherein the electrical neutrality of the compound is ensured by at least one cosmetically acceptable anions An.

19. The dye composition according to claim 18, wherein the at least one direct dye chosen from compounds of formula (I) and the acid addition salts thereof is present in an amount ranging from 0.001% to 20% by weight, relative to the total weight of the dye composition.

20. The dye composition according to claim 19, wherein the at least one direct dye chosen from compounds of formula (I) and the acid addition salts thereof is present in an amount ranging from 0.01% to 10% by weight, relative to the total weight of the dye composition.

21. The dye composition according to claim 18, further comprising at least one color modifier chosen from additional direct dyes different from those of formula (I), and oxidation bases, optionally combined with at least one coupler.

22. The dye composition according to claim 21, wherein the at least one additional direct dye is chosen from cationic and nonionic dyes chosen from nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes and natural dyes, alone or as mixtures.

23. The dye composition according to claim 21, wherein the at least one oxidation base is chosen from o-phenylenediamines, p-phenylenediamines, double bases, o-aminophenols, p-aminophenols, heterocyclic bases, and the acid addition salts thereof.

24. The dye composition according to claim 21, wherein the at least one coupler is chosen from m-aminophenols, m-phenylenediamines, m-diphenols, naphthols, heterocyclic couplers, and the acid addition salts thereof.

25. The dye composition according to claim 18, further comprising at least one oxidizing agent.

26. A process for dyeing keratin fibers, comprising applying to the wet or dry, keratin fibers, a dye composition and leaving the composition on the keratin fibers for a period of time that is sufficient to obtain the desired effect, said dye composition comprising, in a medium suitable for dyeing keratin fibers, at least one direct dye chosen from those of formula (I) and the acid addition salts thereof:

$$\text{Dye1-LK-Dye2} \qquad (I)$$

in which:

Dye1 and Dye2 are such that the compound of formula (I) is not symmetrical, and are chosen from:

Dye 1:

Dye 2:

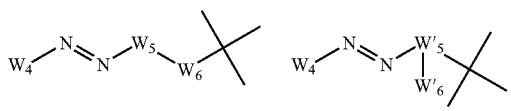

wherein:

$W_1$ and $W_6$, independently of each other, are chosen from —$NR_1$— groups and —O— atoms, in which $R_1$ is chosen from a hydrogen atom and saturated and unsaturated, aromatic and non-aromatic, optionally substituted $C_1$-$C_{20}$ hydrocarbon-based chains, which can form at least one optionally substituted 3- to 7-membered carbon-based rings, optionally interrupted with at least one hetero atom or with at least one group bearing at least one hetero atom;

$W'_1$ and $W'_6$, independently of each other, are chosen from —$NR'_1R'_2$ and —$OR'_3$ groups, in which $R'_1$, $R'_2$ and $R'_3$, independently of each other, are chosen from hydrogen atoms and saturated and unsaturated, aromatic and non-aromatic, optionally substituted $C_1$-$C_{20}$ hydrocarbon-based chains, which can form at least one optionally substituted 3- to 7-membered carbon-based ring, optionally interrupted with at least one hetero atom or with at least one group bearing at least one hetero atom; $R'_1$ and $R'_2$ possibly forming, with the nitrogen atom to which they are attached, an optionally substituted 5- or 7-membered heterocycle optionally comprising another nitrogen or non-nitrogen hetero atom;

the radicals $R_1$ of $W_1$ and $W_6$, together or separately, may form with all or part of the group LK and with the nitrogen atom to which each is attached a saturated or unsaturated, aromatic or non-aromatic, optionally substituted 5- to 7-membered heterocycle;

the radicals $R'_1$, $R'_2$ or $R'_3$ of $W'_1$ and $W'_6$, together or separately, may form, with all or part of the group LK and with the nitrogen or oxygen atom to which each is attached, a saturated or unsaturated, aromatic or non-aromatic, optionally substituted 5- to 7-membered heterocycle;

$W_2$, $W_5$, $W'_2$ and $W'_5$, independently of each other, are chosen from groups of formulae (a), (b), and (c):

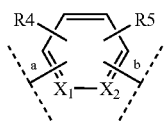 (a)

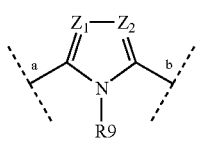 (b)

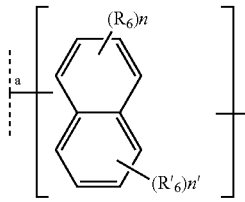 (c)

in which formulae:

$X_1$ is chosen from a nitrogen atom and a group $CR_7$;
$X_2$ is chosen from a nitrogen atom and a group $CR_8$;
$Z_1$ is chosen from a nitrogen atom and a group $CR_{10}$;
$Z_2$ is chosen from a nitrogen atom and a group $CR_{11}$;
$R_4$, $R_5$, $R_6$, $R'_6$, $R_7$, $R_8$, $R_{10}$ and $R_{11}$, independently of each other, are chosen from:
  linear and branched, saturated and unsaturated, aromatic and non-aromatic, optionally substituted $C_1$-$C_{16}$ hydrocarbon-based chains, which can form at least one optionally substituted 3- to 7-membered carbon-based ring, optionally interrupted with at least one hetero atom or with at least one group bearing at least one hetero atom;
hydroxyl groups,
$C_1$-$C_4$ alkoxy groups,
$C_2$-$C_4$ (poly)hydroxyalkoxy groups;
alkoxycarbonyl groups (RO—CO—) in which R is chosen from $C_1$-$C_4$ alkyl radicals,
alkylcarbonyloxy radicals (RCO—O—) in which R is chosen from $C_1$-$C_4$ alkyl radicals;
amino groups,
amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
alkylcarbonylamino groups (RCO—NR—) in which the radicals R, independently of each other, are chosen from $C_1$-$C_4$ alkyl radicals;
carbamoyl groups $((R)_2N—CO)$ in which the radicals R, independently of each other, are chosen from hydrogen atoms and $C_1$-$C_4$ alkyl radicals;
ureido groups $(N(R)_2—CO—NR'—)$ in which the radicals R and R', independently of each other, are chosen from hydrogen atoms and $C_1$-$C_4$ alkyl radicals;
sulfonamide groups $((R)_2N—SO_2—)$ in which the radicals R, independently of each other, are chosen from hydrogen atoms and $C_1$-$C_4$ alkyl radicals;
alkylsulfonylamino groups $(RSO_2—NR'—)$ in which the radicals R and R', independently of each other, are chosen from hydrogen atoms and $C_1$-$C_4$ alkyl radicals;
guanidinium groups $((R')_2N—C(=NH_2^+)—NR—)$ in which the radicals R and R', independently of each other, are chosen from hydrogen atoms and $C_1$-$C_4$ alkyl radicals;
nitro groups;
cyano groups; and
halogen atoms;
wherein $R_4$, $R_5$, $R_7$, $R_8$, $R_{10}$ and $R_{11}$ may each be a hydrogen atom;

wherein $R_4$, $R_5$, $R_6$, $R'_6$, $R_7$, $R_8$, $R_{10}$ and $R_{11}$, independently of each other, may form, with, all or some of the groups $W'_1$ or $W'_6$, or alternatively, all or some of the groups $W_1$ or $W_6$, a saturated or unsaturated, aromatic or non-aromatic, optionally substituted 5- to 7-membered heterocycle;

a bond from $W'_2$ to $W'_1$ or to the group LK, or from $W'_5$ to $W'_6$ or to the group LK;

a is the bond from $W_2$, $W_5$, $W'_2$ or $W'_5$ to the azo group —N=N—;

b is the bond from $W_2$ to $W_1$, from $W_5$ to $W_6$, from $W'_2$ to $W'_1$ or to the group LK, or from $W'_5$ to $W'_6$ or to the group LK;

$R_9$ is chosen from:
- a hydrogen atom,
- linear and branched, saturated and unsaturated, aromatic and non-aromatic, optionally substituted $C_1$-$C_{16}$ hydrocarbon-based chains, which can form at least one optionally substituted 3- to 7-membered carbon-based ring, n and n' are integers and the sum of n and n' is less than or equal to 6;

$W_3$ and $W_4$, independently of each other, are cationic heteroaromatic radicals chosen from those of formulae (1) to (11):

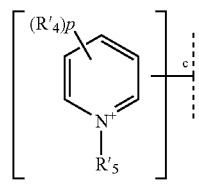
(1)

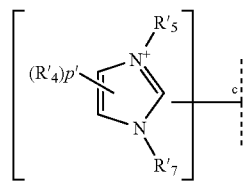
(2)

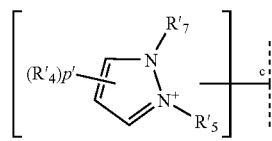
(3)

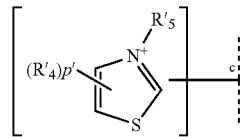
(4)

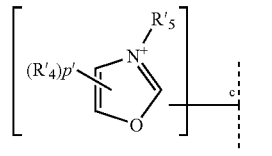
(5)

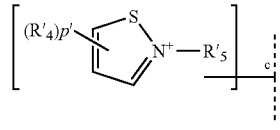
(6)

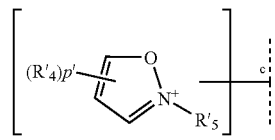
(7)

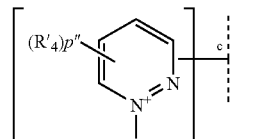
(8)

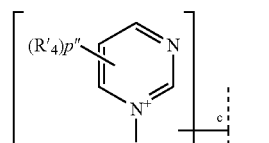
(9)

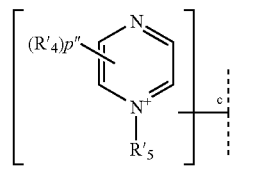
(10)

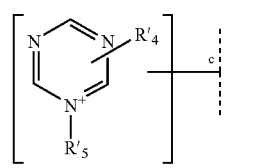
(11)

in which:

$R'_4$, which may be identical or different, substituting the main ring, is chosen from:
- linear and branched, saturated and unsaturated, aromatic and non-aromatic, optionally substituted $C_1$-$C_{16}$ hydrocarbon-based chains, which can form at least one 3- to 6-membered carbon-based ring, optionally interrupted with at least one hetero atom or with at least one group bearing at least one hetero atom;
- hydroxyl groups,
- $C_1$-$C_4$ alkoxy groups,
- $C_2$-$C_4$ (poly)hydroxyalkoxy groups;
- alkoxycarbonyl groups (RO—CO—) in which R is chosen from $C_1$-$C_4$ alkyl radicals,
- alkylcarbonyloxy radicals (RCO—O—) in which R is a $C_1$-$C_4$ alkyl radical;
- amino groups,
- amino groups substituted with at least one $C_1$-$C_4$ alkyl radicals, independently of each other, optionally bearing at least one hydroxyl group, the two alkyl radicals possibly forming, with the nitrogen atom to which they are attached, a 5- or 6-membered heterocycle optionally bearing another nitrogen or non-nitrogen hetero atom;
- alkylcarbonylamino groups (RCO—NR'—) in which the radical R is a $C_1$-$C_4$ alkyl radical and the radical R' is chosen from hydrogen and $C_1$-$C_4$ alkyl radicals;

carbamoyl groups ($(R)_2N$—CO—) in which the radicals R are chosen from, independently of each other, hydrogen atoms or $C_1$-$C_4$ alkyl radicals;

ureido groups ($N(R)_2$—CO—NR'—) in which the radicals R and R', independently of each other, are chosen from hydrogen atoms and $C_1$-$C_4$ alkyl radicals;

sulfonamide groups ($(R)_2N$—$SO_2$—) in which the radicals R, independently of each other, are chosen from hydrogen atoms and $C_1$-$C_4$ alkyl radicals;

alkylsulfonylamino groups ($RSO_2$—NR'—) in which the radicals R and R', independently of each other, are chosen from hydrogen atoms and $C_1$-$C_4$ alkyl radicals;

guanidinium groups ($(R')_2N$—C(=$NH_2^+$)—NR—) in which the radicals R and R', independently of each other, are chosen from hydrogen atoms and $C_1$-$C_4$ alkyl radicals;

nitro groups;

cyano groups; and halogen atoms;

wherein two radicals $R'_4$ borne by two adjacent carbon atoms of the main ring may optionally form an aromatic or non-aromatic, 5- or 6-membered secondary ring, optionally substituted with at least one entity chosen from hydrogen, hydroxyl groups, $C_1$-$C_4$ alkyl radicals, $C_1$-$C_4$ alkoxy radicals, $C_2$-$C_4$ (poly)hydroxyalkoxy radicals, amino radicals, amino radicals substituted with at least one $C_1$-$C_4$ alkyl radical, which may be identical or different, optionally bearing at least one hydroxyl group;

$R'_5$, borne by the quaternized nitrogen atom, is chosen from linear and branched, saturated and unsaturated, aromatic and non-aromatic, optionally substituted $C_1$-$C_{16}$ hydrocarbon-based chains, which can form an optionally substituted 3- to 7-membered carbon-based ring, optionally interrupted with at least one hetero atom or with at least one group bearing at least one hetero atom; the radical $R'_5$ is such that the atom directly linked to the quaternized nitrogen atom is a carbon atom;

$R'_7$ is chosen from optionally substituted $C_1$-$C_4$ alkyl radicals; optionally substituted phenyl radicals; and optionally substituted benzyl radicals;

the bond c links the cationic radical defined by formulae (1) to (11) to the azo group, the bond may be on the main or secondary ring;

p is an integer ranging from 0 to 4, p' is an integer ranging from 0 to 2, and p" is an integer ranging from 0 to 3;

when the main ring does not bear the maximum number of substituents, then the unsubstituted position(s) bear(s) a nitrogen atom; with the condition that at least one of the two groups $W_3$ and $W_4$ are not chosen from unsubstituted imidazolium groups;

LK is chosen from saturated and unsaturated, linear and branched, cyclic and non-cyclic, aromatic and non-aromatic, optionally substituted $C_2$-$C_{40}$ hydrocarbon-based chains, optionally interrupted with at least one hetero atom or group comprising at least one hetero atom, with the proviso that the group LK does not comprise any nitro, nitroso or peroxo groups or bonds wherein the LK does not bear a cationic charge; LK may end with a hetero atom or group bearing at least one hetero atom, if LK is linked to $W'_2$ or $W'_5$; LK may end with a group bearing at least one hetero atom chosen from —CO— and —$SO_2$— if LK is linked to $W_6$ or $W_1$; and wherein the electrical neutrality of the compound is ensured by at least one cosmetically acceptable anions An.

27. A multi-compartment kit comprising at least one first compartment comprising at least one dye composition comprising, in a medium suitable for dyeing keratin fibers, at least one direct dye chosen from those of formula (I) and the acid addition salts thereof:

Dye1-LK-Dye2     (I)

in which:

Dye1 and Dye2 are such that the compound of formula (I) is not symmetrical, and are chosen from:

Dye 1:

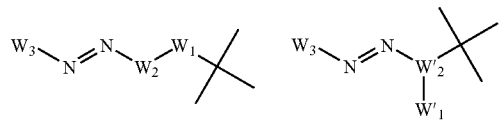

Dye 2:

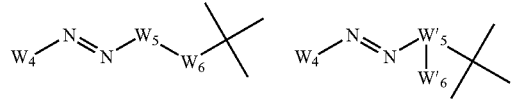

wherein:

$W_1$ and $W_6$, independently of each other, are chosen from —$NR_1$— groups and —O— atoms, in which $R_1$ is chosen from a hydrogen atom and saturated and unsaturated, aromatic and non-aromatic, optionally substituted $C_1$-$C_{20}$ hydrocarbon-based chains, which can form at least one optionally substituted 3- to 7-membered carbon-based rings, optionally interrupted with at least one hetero atom or with at least one group bearing at least one hetero atom;

$W'_1$ and $W'_6$, independently of each other, are chosen from —$NR'_1R'_2$ and —$OR'_3$ groups, in which $R'_1$, $R'_2$ and $R'_3$, independently of each other, are chosen from hydrogen atoms and saturated and unsaturated, aromatic and non-aromatic, optionally substituted $C_1$-$C_{20}$ hydrocarbon-based chains, which can form at least one optionally substituted 3- to 7-membered carbon-based ring, optionally interrupted with at least one hetero atom or with at least one group bearing at least one hetero atom; $R'_1$ and $R'_2$ possibly forming, with the nitrogen atom to which they are attached, an optionally substituted 5- or 7-membered heterocycle optionally comprising another nitrogen or non-nitrogen hetero atom;

the radicals $R_1$ of $W_1$ and $W_6$, together or separately, may form with all or part of the group LK and with the nitrogen atom to which each is attached a saturated or unsaturated, aromatic or non-aromatic, optionally substituted 5- to 7-membered heterocycle;

the radicals $R'_1$, $R'_2$ or $R'_3$ of $W'_1$ and $W'_6$, together or separately, may form, with all or part of the group LK and with the nitrogen or oxygen atom to which each is attached, a saturated or unsaturated, aromatic or non-aromatic, optionally substituted 5- to 7-membered heterocycle;

$W_2$, $W_5$, $W'_2$ and $W'_5$, independently of each other, are chosen from groups of formulae (a), (b), and (c):

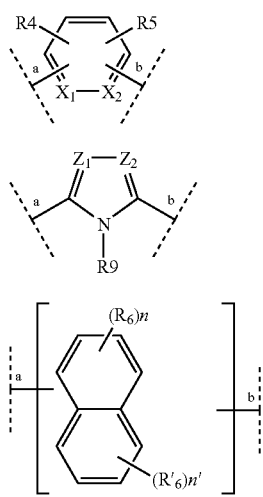

in which formulae:

$X_1$ is chosen from a nitrogen atom and a group $CR_7$;
$X_2$ is chosen from a nitrogen atom and a group $CR_8$;
$Z_1$ is chosen from a nitrogen atom and a group $CR_{10}$;
$Z_2$ is chosen from a nitrogen atom and a group $CR_{11}$;
$R_4$, $R_5$, $R_6$, $R'_6$, $R_7$, $R_8$, $R_{10}$ and $R_{11}$, independently of each other, are chosen from:

- linear and branched, saturated and unsaturated, aromatic and non-aromatic, optionally substituted $C_1$-$C_{16}$ hydrocarbon-based chains, which can form at least one optionally substituted 3- to 7-membered carbon-based ring, optionally interrupted with at least one hetero atom or with at least one group bearing at least one hetero atom;
- hydroxyl groups,
- $C_1$-$C_4$ alkoxy groups,
- $C_2$-$C_4$ (poly)hydroxyalkoxy groups;
- alkoxycarbonyl groups (RO—CO—) in which R is chosen from $C_1$-$C_4$ alkyl radicals,
- alkylcarbonyloxy radicals (RCO—O—) in which R is chosen from $C_1$-$C_4$ alkyl radicals;
- amino groups,
- amino groups substituted with at least one $C_1$-$C_4$ alkyl radical, which may be identical or different, optionally bearing at least one hydroxyl group, the alkyl radicals possibly forming, with the nitrogen atom to which they are attached, a 5- or 6-membered heterocycle optionally bearing another nitrogen or non-nitrogen hetero atom;
- alkylcarbonylamino groups (RCO—NR—) in which the radicals R, independently of each other, are chosen from $C_1$-$C_4$ alkyl radicals;
- carbamoyl groups (($R)_2$N—CO) in which the radicals R, independently of each other, are chosen from hydrogen atoms and $C_1$-$C_4$ alkyl radicals;
- ureido groups (N(R)$_2$—CO—NR'—) in which the radicals R and R', independently of each other, are chosen from hydrogen atoms and $C_1$-$C_4$ alkyl radicals;
- sulfonamide groups (($R)_2$N—SO$_2$—) in which the radicals R, independently of each other, are chosen from hydrogen atoms and $C_1$-$C_4$ alkyl radicals;
- alkylsulfonylamino groups (RSO$_2$—NR'—) in which the radicals R and R', independently of each other, are chosen from hydrogen atoms and $C_1$-$C_4$ alkyl radicals;
- guanidinium groups ((R')$_2$N—C(=NH$_2^+$)—NR—) in which the radicals R and R', independently of each other, are chosen from hydrogen atoms and $C_1$-$C_4$ alkyl radicals;
- nitro groups;
- cyano groups; and
- halogen atoms;

wherein $R_4$, $R_5$, $R_7$, $R_8$, $R_{10}$ and $R_{11}$ may each be a hydrogen atom;

wherein $R_4$, $R_5$, $R_6$, $R'_6$, $R_7$, $R_8$, $R_{10}$ and $R_{11}$, independently of each other, may form, with, all or some of the groups $W'_1$ or $W'_6$, or alternatively, all or some of the groups $W_1$ or $W_6$, a saturated or unsaturated, aromatic or non-aromatic, optionally substituted 5- to 7-membered heterocycle;

a bond from $W'_2$ to $W'_1$ or to the group LK, or from $W'_5$ to $W'_6$ or to the group LK;

a is the bond from $W_2$, $W_5$, $W'_2$ or $W'_5$ to the azo group —N=N—;

b is the bond from $W_2$ to $W_1$, from $W_5$ to $W_6$, from $W'_2$ to $W'_1$ or to the group LK, or from $W'_5$ to $W'_6$ or to the group LK;

$R_9$ is chosen from:

- a hydrogen atom,
- linear and branched, saturated and unsaturated, aromatic and non-aromatic, optionally substituted $C_1$-$C_{16}$ hydrocarbon-based chains, which can form at least one optionally substituted 3- to 7-membered carbon-based ring, n and n' are integers and the sum of n and n' is less than or equal to 6;

$W_3$ and $W_4$, independently of each other, are cationic heteroaromatic radicals chosen from those of formulae (1) to (11):

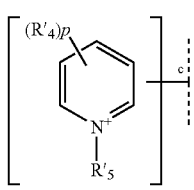

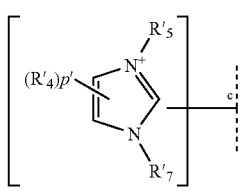

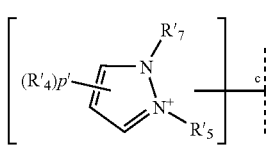

-continued

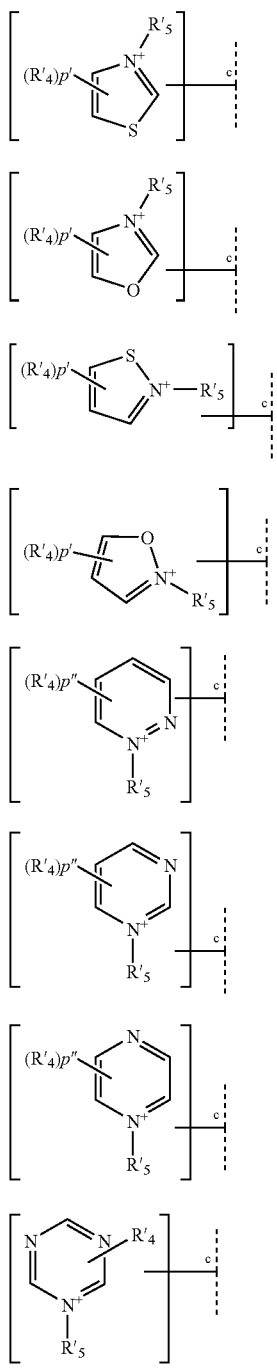

in which:

R'₄, which may be identical or different, substituting the main ring, is chosen from:
  linear and branched, saturated and unsaturated, aromatic and non-aromatic, optionally substituted $C_1$-$C_{16}$ hydrocarbon-based chains, which can form at least one 3- to 6-membered carbon-based ring, optionally interrupted with at least one hetero atom or with at least one group bearing at least one hetero atom;
  hydroxyl groups,
  $C_1$-$C_4$ alkoxy groups,
  $C_2$-$C_4$ (poly)hydroxyalkoxy groups;
  alkoxycarbonyl groups (RO—CO—) in which R is chosen from $C_1$-$C_4$ alkyl radicals,
  alkylcarbonyloxy radicals (RCO—O—) in which R is a $C_1$-$C_4$ alkyl radical;
  amino groups,
  amino groups substituted with at least one $C_1$-$C_4$ alkyl radicals, independently of each other, optionally bearing at least one hydroxyl group, the two alkyl radicals possibly forming, with the nitrogen atom to which they are attached, a 5- or 6-membered heterocycle optionally bearing another nitrogen or non-nitrogen hetero atom;
  alkylcarbonylamino groups (RCO—NR'—) in which the radical R is a $C_1$-$C_4$ alkyl radical and the radical R' is chosen from hydrogen and $C_1$-$C_4$ alkyl radicals;
  carbamoyl-groups ((R)₂N—CO—) in which the radicals R are chosen from, independently of each other, hydrogen atoms or $C_1$-$C_4$ alkyl radicals;
  ureido groups (N(R)₂—CO—NR'—) in which the radicals R and R', independently of each other, are chosen from hydrogen atoms and $C_1$-$C_4$ alkyl radicals;
  sulfonamide groups ((R)₂N—SO₂—) in which the radicals R, independently of each other, are chosen from hydrogen atoms and $C_1$-$C_4$ alkyl radicals;
  alkylsulfonylamino groups (RSO₂—NR'—) in which the radicals R and R', independently of each other, are chosen from hydrogen atoms and $C_1$-$C_4$ alkyl radicals;
  guanidinium groups ((R')₂N—C(=NH₂⁺)—NR—) in which the radicals R and R', independently of each other, are chosen from hydrogen atoms and $C_1$-$C_4$ alkyl radicals;
  nitro groups;
  cyano groups; and
  halogen atoms;
  wherein two radicals R'₄ borne by two adjacent carbon atoms of the main ring may optionally form an aromatic or non-aromatic, 5- or 6-membered secondary ring, optionally substituted with at least one entity chosen from hydrogen, hydroxyl groups, $C_1$-$C_4$ alkyl radicals, $C_1$-$C_4$ alkoxy radicals, $C_2$-$C_4$ (poly)hydroxyalkoxy radicals, amino radicals, amino radicals substituted with at least one $C_1$-$C_4$ alkyl radical, which may be identical or different, optionally bearing at least one hydroxyl group;

R'₅, borne by the quaternized nitrogen atom, is chosen from linear and branched, saturated and unsaturated, aromatic and non-aromatic, optionally substituted $C_1$-$C_{16}$ hydrocarbon-based chains, which can form an optionally substituted 3- to 7-membered carbon-based ring, optionally interrupted with at least one hetero atom or with at least one group bearing at least one hetero atom; the radical R'₅ is such that the atom directly linked to the quaternized nitrogen atom is a carbon atom;

R'₇ is chosen from optionally substituted $C_1$-$C_4$ alkyl radicals; optionally substituted phenyl radicals; and optionally substituted benzyl radicals;

the bond c links the cationic radical defined by formulae (1) to (11) to the azo group; the bond may be on the main or secondary ring;

p is an integer ranging from 0 to 4, p' is an integer ranging from 0 to 2, and p" is an integer ranging from 0 to 3;

when the main ring does not bear the maximum number of substituents, then the unsubstituted position(s) bear(s) a nitrogen atom; with the condition that at least one of the two groups $W_3$ and $W_4$ are not chosen from unsubstituted imidazolium groups;

LK is chosen from saturated and unsaturated, linear and branched, cyclic and non-cyclic, aromatic and non-aromatic, optionally substituted $C_2$-$C_{40}$ hydrocarbon-based chains, optionally interrupted with at least one hetero atom or group comprising at least one hetero atom, with the proviso that the group LK does not comprise any nitro, nitroso or peroxo groups or bonds wherein the LK does not bear a cationic charge; LK may end with a hetero atom or group bearing at least one hetero atom, if LK is linked to $W'_2$ or $W'_5$; LK may end with a group bearing at least one hetero atom chosen from —CO— and —$SO_2$— if LK is linked to $W_6$ or $W_1$; and wherein the electrical neutrality of the compound is ensured by at least one cosmetically acceptable anions An.

at least one second compartment comprising at least one oxidizing composition comprising at least one oxidizing agent.

* * * * *

UNITED STATES PATENT AND TRADEMARK OFFICE
CERTIFICATE OF CORRECTION

PATENT NO. : 7,282,069 B2 Page 1 of 1
APPLICATION NO. : 11/159237
DATED : October 16, 2007
INVENTOR(S) : Andrew Greaves et al.

It is certified that error appears in the above-identified patent and that said Letters Patent is hereby corrected as shown below:

On the title page, item (57), lines 3-4, "comprising the the compounds" should read --comprising the compounds--.

In claim 5, column 51, line 49, "$C_1$-$C_4$-alkyl" should read --$C_1$-$C_4$ alkyl--.

In claim 16, column 57, line 54, "identical/or" should read --identical or--.

In claim 18, column 59, line 52, "—$W'_2$" should read --$W'_2$--.

In claim 18, column 60, line 65, "a nitro groups;" should read --nitro groups;--.

In claim 27, column 74, line 19, "carbamoyl-groups" should read --carbamoyl groups--.

In claim 27, column 76, line 5, "$W_1$; and" should read --$W_1$;--.

In claim 27, column 76, line 8, "An." should read --An; and--.

Signed and Sealed this

Twenty-fifth Day of December, 2007

JON W. DUDAS
*Director of the United States Patent and Trademark Office*